(12) United States Patent　　　　　(10) Patent No.:　US 12,683,019 B2

Kashima　　　　　　　　　　　　　　　(45) Date of Patent:　　Jul. 14, 2026

(54) BIOLOGICAL INFORMATION MONITORING APPARATUS, BIOLOGICAL INFORMATION MONITORING SYSTEM, RECORDING MEDIUM, AND BIOLOGICAL INFORMATION MONITORING METHOD

(71) Applicant: Konica Minolta, Inc., Tokyo (JP)

(72) Inventor: Koji Kashima, Higashiyamato (JP)

(73) Assignee: KONICA MINOLTA, INC., Tokyo (JP)

( * ) Notice: Subject to any disclaimer, the term of this patent is extended or adjusted under 35 U.S.C. 154(b) by 175 days.

(21) Appl. No.: 18/321,335

(22) Filed: May 22, 2023

(65) Prior Publication Data

US 2023/0395251 A1　　Dec. 7, 2023

(30) Foreign Application Priority Data

Jun. 1, 2022　　(JP) ................................. 2022-089319

(51) Int. Cl.
　*G16H 40/63*　　　(2018.01)
　*A61B 5/00*　　　(2006.01)
(52) U.S. Cl.
　CPC ........... *G16H 40/63* (2018.01); *A61B 5/7221* (2013.01); *A61B 5/742* (2013.01)
(58) Field of Classification Search
　None
　See application file for complete search history.

(56) References Cited

U.S. PATENT DOCUMENTS

| | | | | |
|---|---|---|---|---|
| 2008/0188733 A1* | 8/2008 | Al-Ali | ..................... | A61B 5/08 |
| | | | | 600/509 |
| 2010/0094096 A1* | 4/2010 | Petruzzelli | .............. | G16Z 99/00 |
| | | | | 600/300 |
| 2016/0302741 A1* | 10/2016 | Miyamura | ............. | A61B 5/742 |
| 2016/0342827 A1* | 11/2016 | Kaiami | ..................... | A61B 5/02 |
| 2018/0153482 A1* | 6/2018 | Watanabe | .......... | A61B 5/02055 |
| 2019/0374169 A1* | 12/2019 | Inoue | ..................... | A61B 8/468 |
| 2019/0374170 A1* | 12/2019 | Inoue | ..................... | A61B 5/743 |
| 2019/0383928 A1* | 12/2019 | Kuwahara | ............. | G01S 13/343 |
| 2020/0029832 A1* | 1/2020 | Kogure | ................ | A61B 5/4809 |
| 2021/0038087 A1* | 2/2021 | Heneghan | ............ | A61B 5/0826 |
| 2021/0077031 A1* | 3/2021 | Fukunaga | .............. | G06F 3/015 |

(Continued)

FOREIGN PATENT DOCUMENTS

| | | |
|---|---|---|
| JP | 2010-120493 A | 6/2010 |
| JP | 2016-142586 A | 8/2016 |

(Continued)

OTHER PUBLICATIONS

Bodin et al., Improving the Information reliability in Medical Information System based on Multi-Agent Technology, 21st International Conference On Micro/ Nanotechnologies and Electron Devices EDM 2020.*

(Continued)

*Primary Examiner* — David J Stoltenberg
(74) *Attorney, Agent, or Firm* — LUCAS & MERCANTI, LLP

(57) ABSTRACT

A biological information monitoring apparatus, including a hardware processor that: obtains biological information on a patient; determines a reliability degree of the biological information; and causes a display to display information related to a reason of the determination result.

14 Claims, 18 Drawing Sheets

(56) References Cited

U.S. PATENT DOCUMENTS

| | | | | |
|---|---|---|---|---|
| 2021/0272278 A1* | 9/2021 | Terai | .................... | G16H 15/00 |
| 2022/0018864 A1* | 1/2022 | Meguro | ................ | G06T 7/0012 |
| 2022/0148735 A1* | 5/2022 | Shige | .................... | G16H 30/40 |
| 2022/0280063 A1* | 9/2022 | Ohtsuki | ............... | A61B 5/7264 |
| 2022/0379057 A1* | 12/2022 | Eger | .................... | G16H 40/40 |
| 2023/0420087 A1* | 12/2023 | Fukatani | ............... | A61B 5/742 |
| 2025/0268540 A1* | 8/2025 | Kiani | ................... | A61B 5/0022 |

FOREIGN PATENT DOCUMENTS

| | | | | | |
|---|---|---|---|---|---|
| JP | 6697985 B2 | | 5/2020 | | |
| JP | 2021-041088 A | | 3/2021 | | |
| JP | 2023-41158 A | * | 9/2021 | ........... | A61B 5/0245 |
| KR | 2023-0026884 A | * | 8/2021 | .............. | A61B 5/11 |
| WO | WO 2020/071374 A1 | * | 10/2019 | .............. | A61B 5/16 |

OTHER PUBLICATIONS

Mavrogiorgou et al. Delivering Reliability of Data Sources in IoT Healthcare Ecosystems, 2019 25th Conference of Open Innovations Association (FRUCT).*

Dou et al., Full Respiration Rate Monitoring Exploiting Doppler Information with Commodity Wi-Fi Devices, Sensors 2021, 21, 3505. https://doi.org/10.3390/s21103505.*

Sokullo et al., Wireless Patient Monitoring System, 2010 Fourth International Conference of Sensor Technologies and Applications.*

Office Action, dated Nov. 25, 2025, which was issued for the corresponding Japanese Patent Application No. 2022-089319, 9 pages, with English translation.

Office Action issued for the related Japanese patent application No. 2022-089319, mailed Mar. 3, 2026, with English translation, 7 pages.

* cited by examiner

NURSE STATION

STATION SERVER
10

13

20 EXTERNAL HDD

21 UPS

22 PRINTER

100

PATIENT ROOM

41 PULSE OXIMETER

42 RESPIRATION SENSOR

BEDSIDE TERMINAL
30

51 IC CARD

52 MEASURING INSTRUMENT

60 MOBILE TERMINAL

FIG.4

| OCCURRING EVENT | REASON OF LOW RELIABILITY DEGREE | ADVERSE EFFECT | DISPLAY METHOD | MEASURES | POSSIBILITY OF BEING CAUSED BY LIVING BODY | POSSIBILITY OF BEING CAUSED BY WHAT IS OTHER THAN LIVING BODY |
|---|---|---|---|---|---|---|
| DEGRADATION IN S/N RATIO | WIRELESS RECEIVED SIGNAL IS TOO LARGE WITH RESPECT TO RECEPTION PERFORMANCE OF APPARATUS. | SIGNAL DEFORMATION | • EXCESSIVE INPUT DISPLAY | • KEEP RADIO WAVE SENSOR AWAY FROM PERSON | O | O |
| | WIRELESS RECEIVED SIGNAL IS TOO SMALL WITH RESPECT TO RECEPTION PERFORMANCE OF APPARATUS. | SIGNAL CONTAINS NOISE | • TOO LOW INPUT DISPLAY • ANTENNA DISPLAY | • BRING RADIO WAVE SENSOR CLOSE TO PERSON • REMOVE OBSTACLE | O | O |
| | PHASE VARIATION IS TOO SMALL. | SIGNAL CONTAINS NOISE | • BED LEAVING DISPLAY • INFREQUENT RESPIRATION/APNEIC DISPLAY | • CONFIRM STATE OF MEASUREMENT TARGET | O | X |
| OUT OF RANGE | MEASURED VALUE IS TOO LARGE OR TOO SMALL WITH RESPECT TO MEASUREMENT RANGE OF APPARATUS. | INCREASE IN MEASUREMENT ERROR | • BRADYPNEA/TACHYPNEA DISPLAY | • CONFIRM STATE OF MEASUREMENT TARGET • CHANGE THRESHOLD | O | O |
| LARGE VARIANCE | MEASURED VALUE VARIANCE IS TOO LARGE. | ERRONEOUS RECOGNITION OF MEASUREMENT VALUE | • MEASURED VALUE TIME-SERIES DISPLAY • SPECTRUM DISPLAY, HISTOGRAM DISPLAY • STATISTICS DISPLAY (STANDARD DEVIATION, VARIATION COEFFICIENT, ETC.) | • DETERMINE STATE BASED ON PERIOD AND MAGNITUDE OF VARIATION | O | X |
| MULTIPLE ELEMENTS | THERE ARE MULTIPLE MEASUREMENT CANDIDATES. | ERRONEOUS MEASUREMENT TARGET | • MEASUREMENT CANDIDATE TWO-DIMENSIONAL DISPLAY | • SELECT TARGET INTENDED TO BE MEASURED | O | X |
| BODY MOTION | MEASURED VALUE VARIANCE IS LARGE, AND HAS NO PERIODICITY | SIGNAL DEFORMATION, SIGNAL CONTAINS NOISE | • BODY MOTION DISPLAY | • WAIT UNTIL BODY MOTION SETTLES | O | X |

FIG.6

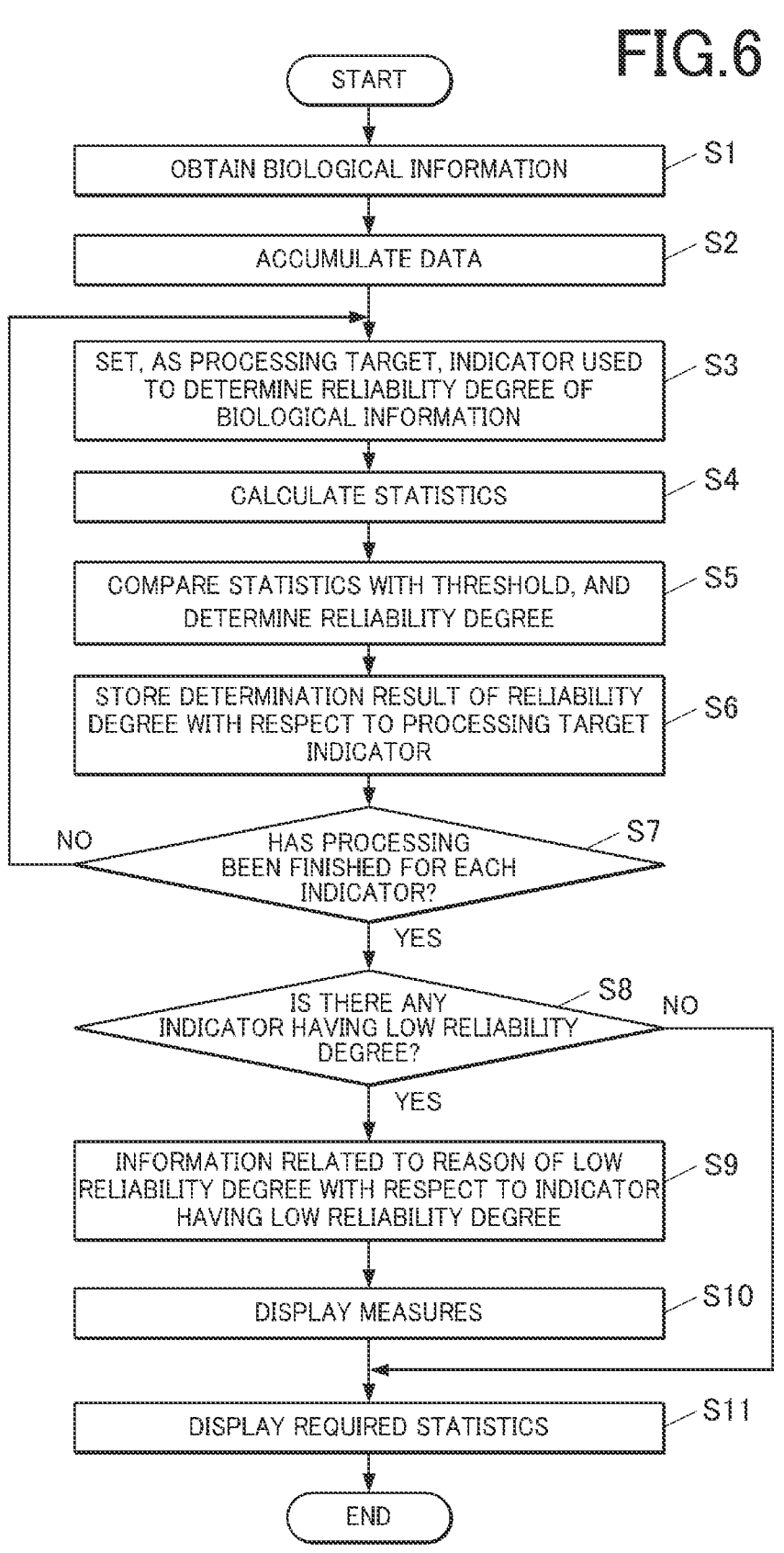

START

OBTAIN BIOLOGICAL INFORMATION — S1

ACCUMULATE DATA — S2

SET, AS PROCESSING TARGET, INDICATOR USED TO DETERMINE RELIABILITY DEGREE OF BIOLOGICAL INFORMATION — S3

CALCULATE STATISTICS — S4

COMPARE STATISTICS WITH THRESHOLD, AND DETERMINE RELIABILITY DEGREE — S5

STORE DETERMINATION RESULT OF RELIABILITY DEGREE WITH RESPECT TO PROCESSING TARGET INDICATOR — S6

HAS PROCESSING BEEN FINISHED FOR EACH INDICATOR? — S7
NO
YES

IS THERE ANY INDICATOR HAVING LOW RELIABILITY DEGREE? — S8
NO
YES

INFORMATION RELATED TO REASON OF LOW RELIABILITY DEGREE WITH RESPECT TO INDICATOR HAVING LOW RELIABILITY DEGREE — S9

DISPLAY MEASURES — S10

DISPLAY REQUIRED STATISTICS — S11

END

FIG.7

| INDICATOR | RELIABILITY DEGREE | | EXAMPLE OF DISPLAY METHOD IN CASE OF LOW RELIABILITY DEGREE |
|---|---|---|---|
| | HIGH | LOW | |
| SIGNAL RECEIVED POWER | WITHIN APPROPRIATE RANGE | TOO LOW | REPRESENT THAT RECEIVED SIGNAL IS LOW, BY THE NUMBER OF ANTENNAS. DISPLAY POSSIBILITY THAT DISTANCE TO MEASUREMENT TARGET IS LARGE, OR OBSTACLE IS PRESENT |
| SIGNAL RECEIVED POWER | WITHIN APPROPRIATE RANGE | TOO HIGH | DISPLAY CROSS MARK AND THE LIKE IN ADDITION TO THREE ANTENNAS. |
| DISTANCE | CLOSE TO TARGET POINT | DISTANT FROM TARGET POINT | DISPLAY DISTANCE AND ANGLE OF MEASUREMENT POSITION, THUS DISPLAYING THAT IT IS DISTANT FROM REFERENCE POSITION (POSITION HAVING HIGH POSSIBILITY OF PRESENCE OF HUMAN BODY). |
| AMPLITUDE OF RESPIRATION SIGNAL | LARGE (DEEP RESPIRATION) | SMALL (SHALLOW RESPIRATION) | DISPLAY THAT RESPIRATION IS TOO SHALLOW. DISPLAY RESPIRATION WAVEFORM, ADDITIONALLY WITH THRESHOLD FOR DETERMINING THAT RESPIRATION IS SHALLOW. |
| RESPIRATION RATE | WITHIN MEASUREMENT ASSURANCE RANGE | OUT OF MEASUREMENT ASSURANCE RANGE | DISPLAY MEASUREMENT VALUE ITSELF IN HIGHLIGHTED MANNER. |
| VARIATION IN RESPIRATION RATE | SMALL | LARGE | DISPLAY THAT VARIATION IS LARGE. DISPLAY DEGREE OF VARIATION IN GRASPABLE MANNER USING STATISTICS. |
| THE NUMBER OF MEASUREMENT TARGETS | ONE | PLURALITY | DISPLAY DETECTED POSITION OF MEASUREMENT TARGET. |

XX TARO — 72

XX TARO — 72

73

77     76     75     80

42    93    14    CI95% ±5

40 – 120    77 – 100    10 – 30

77a     76a     75a

335

| 71 | A1234567890 |
| 72 | XX TARO |

81

77    76

42    93    — —

73

75

40 – 120    77 – 100    10 – 30

77a    76a    75a

336

| 71 | A1234567890 |
| 72 | XX TARO |

74

77    76

42    93    35

73

75

40 – 120    77 – 100    10 – 30

77a    76a    75a

337A

337B

BIOLOGICAL INFORMATION MONITORING APPARATUS, BIOLOGICAL INFORMATION MONITORING SYSTEM, RECORDING MEDIUM, AND BIOLOGICAL INFORMATION MONITORING METHOD

REFERENCE TO RELATED APPLICATIONS

The entire disclosure of Japanese Patent Application No. 2022-089319, filed on Jun. 1, 2022, including description, claims, drawings and abstract is incorporated herein by reference in its entirety.

TECHNICAL FIELD

The present invention relates to a biological information monitoring apparatus, a biological information monitoring system, a recording medium, and a biological information monitoring method.

DESCRIPTION OF THE RELATED ART

Conventionally, a biological information monitoring system has been used that continuously measures biological information, such as the respiratory rate, percutaneous oxygen saturation ($SpO_2$), and pulse rate, from a patient in a hospital, and monitors presence or absence of an abnormality. A healthcare worker, such as a nurse, verifies biological information measurement data displayed on a bedside terminal provided on a bedside, or a monitoring apparatus in a nurse station.

As a biosignal detection apparatus that detects a biosignal from a human body, an apparatus has been proposed that calculates an estimated distance from the human body based on the detected signal output from a radio wave sensor, determines the reliability degree of the biosignal based on the estimated distance, and stops outputting the biosignal if the reliability degree is low (see JP 2010-120493A).

Furthermore, a technique has been proposed where a biological information output apparatus determines the reliability of biological information measured from a subject, outputs the biological information if the reliability is determined to be high, and does not output the biological information if the reliability is determined to be low, and the apparatus determines that the reliability is low if the subject is not in a bed rest state (see JP6697985B).

As described above, according to the conventional art, what stops outputting biological information if the reliability degree of the biological information decreases has been used.

SUMMARY OF THE INVENTION

Unfortunately, there is a problem that if the reason of determining that the reliability degree of the biological information is low is unknown, a user cannot determine what to behave next in order to improve the reliability degree. In actual operation, it is required to notify the user of the reason of reduction in reliability degree, and provide information to improve the situations, and environment.

The present invention has been made in view of the problem in the conventional art described above, and has an object to provide information for recognizing the reason of the determination result in determination of the reliability degree of biological information.

To achieve at least one of the abovementioned objects, according to an aspect of the present invention, a biological information monitoring apparatus reflecting one aspect of the present invention is a biological information monitoring apparatus, including a hardware processor that:

obtains biological information on a patient;

determines a reliability degree of the biological information; and causes a display to display information related to a reason of the determination result.

To achieve at least one of the abovementioned objects, according to another aspect of the present invention, a biological information monitoring system reflecting one aspect of the present invention is a biological information monitoring system, including a hardware processor that:

obtains biological information on a patient;

determines a reliability degree of the biological information; and causes a display to display information related to a reason of the determination result.

To achieve at least one of the abovementioned objects, according to another aspect of the present invention, a recording medium reflecting one aspect of the present invention is a computer-readable non-transitory recording medium storing a biological information monitoring program that causes a computer to achieve:

an obtainment function of obtaining biological information on a patient;

a reliability degree determination function of determining a reliability degree of the biological information; and a display control function of causing a display to display information related to a reason of a determination result by the reliability degree determination function.

To achieve at least one of the abovementioned objects, according to another aspect of the present invention, a biological information monitoring method reflecting one aspect of the present invention is a biological information monitoring method, including:

obtaining biological information on a patient;

determining a reliability degree of the biological information; and causing a display to display information related to a reason of a determination result by the reliability degree determining.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein:

FIG. 4 shows a classification example of reasons of low reliability degrees:

FIG. 6 is a flowchart showing a reliability degree determination reason display process executed by the bedside terminal:

FIG. 7 shows an example of a condition for determining that the reliability degree is high or low, and display methods if the reliability degree is determined to be low, with respect to each indicator used to determine the reliability degree:

FIG. 13A shows an example of a biological information display screen including the variation:

FIG. 13B shows an example of a biological information display screen including the variation:

DETAILED DESCRIPTION

Hereinafter, an embodiment of the present invention is described with reference to the drawings. However, the scope of the invention is not limited to the disclosed embodiments or illustrated examples.

[Configuration of Biological Information Monitoring System]

Figure 1:
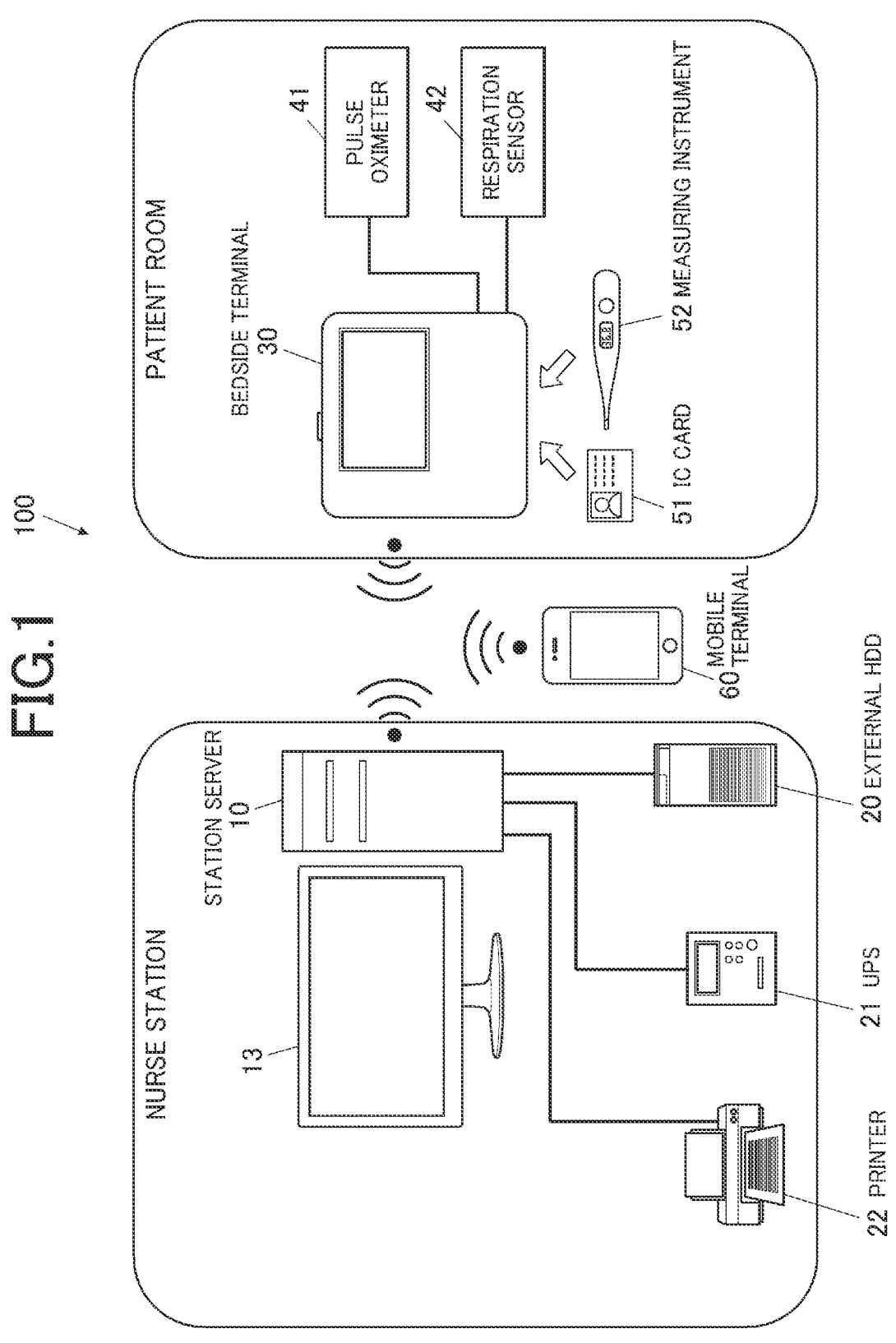
FIG. 1 shows a system configuration of a biological information monitoring system.

FIG. 1 shows a system configuration of a biological information monitoring system 100.

As shown in FIG. 1, the biological information monitoring system 100 includes: a station server 10 provided in a nurse station; a bedside terminal 30 serving as a biological information monitoring apparatus provided at each of beds in patient rooms; and a mobile terminal 60 carried by a healthcare worker, such as a nurse. The biological information monitoring system 100 is used in a medical facility, such as a hospital. The station server 10, the bedside terminal 30, and the mobile terminal 60 are capable of data communication with each other by wireless communication. Preferably, the wireless communication in the medical facility is in the sub-GHz band with relatively small interference at frequencies used for communication. However, there is no limitation to this. Note that the numbers of bedside terminals 30 and mobile terminals 60 are not particularly limited.

The station server 10 centrally manages measurement data (biological information) on each patient collected by the bedside terminal 30. A display 13 of the station server 10 displays a monitoring screen that includes biological information on multiple patients. On the monitoring screen, there are arranged multiple display areas corresponding to the patients of the respective bedside terminals 30. In the nurse station, changes in the condition of the patients can be grasped through the station server 10. The station server 10 may transmit measurement data on each patient to a cloud server connected via a communication network, and allow the measurement data to be managed in the cloud server.

The biological information is various pieces of physiological and anatomical information emitted by living bodies. The biological information may include, for example, the respiratory rate, percutaneous oxygen saturation (SpO$_2$), pulse rate, heart rate, and minute ventilation volume (V$_E$).

The monitoring screen is a screen displayed for monitoring the biological information on the patient. Monitoring means continuous monitoring of target information (biological information on the patient, and the like). The monitoring also includes recording of the target information over time, and detection of an abnormality.

An external hard disk drive (HDD) 20, an uninterruptible power supply (UPS) 21, and a printer 22 are connected to the station server 10.

The external HDD 20 stores data, such as biological information on each patient, managed by the station server 10.

The UPS 21 is an apparatus that internally includes a device that accumulates power, such as a secondary battery, and can supply power at a predetermined output for a prescribed time period even in case power supply from the outside is interrupted owing to a power outage or the like.

The printer 22 performs printing on a sheet, and prints various measurement data items, patient information and the like displayed on the display 13 of the station server 10.

The bedside terminal 30 is installed at a bedside of each patient, obtains biological information on the corresponding patient from the pulse oximeter 41, and a respiration sensor 42, and displays a measurement result. The bedside terminal 30 reads an IC card 51, and obtains identification information on a healthcare worker, and obtains biological information on the patient from a measuring instrument 52, such as a thermometer, in conformity with near field communication (NFC). The bedside terminal 30 transmits a measurement result of the biological information to the station server 10.

The pulse oximeter 41 is an instrument that is worn at a site of a living body, such as a finger tip of a patient, and measures biological information, such as SpO$_2$, and pulse rate.

The respiration sensor 42 is an instrument that measures biological information, such as the respiratory waveform, the number of respirations per minute. The respiration sensor 42 is a non-contact measuring instrument. The non-contact type is for a method of collecting information without direct contact of the measuring instrument (the respiration sensor 42 or the like) with the patient. What measures biological information by the non-contact method may be a radio wave sensor, a piezoelectric sensor, etc.

The radio wave sensor emits radio waves, receives radio waves reflected by a measurement target object, and detects the movement speed (motion) of the measurement target object, based on occurrence of change in frequency between the transmitted waves, and the reflected waves. The radio wave sensor may be a microwave sensor, a millimeter-wave sensor, or the like. The radio wave sensor encompasses types of a frequency modulated continuous wave (FMCW) sensor, a continuous wave (CW) sensor, etc.

The FMCW scheme is a scheme of transmitting a signal modulated so that the frequency linearly increases with a lapse of time. The FMCW scheme can separate the signal in a distance direction in accordance with the width of the frequency band to be used. Accordingly, this scheme can measure not only the motion of the target object but also the distance from the target object.

The CW scheme is a scheme of transmitting a signal that is not modulated, and has a single frequency. The CW scheme has no band width, and cannot separate the signal in the distance direction.

The piezoelectric sensor detects respiration, heartbeats, and the like from a faint pressure on the body surface, by outputting the pressure as an electric signal.

The mobile terminal 60 displays measurement data (biological information) on each patient transmitted from the station server 10, or the bedside terminal 30. Accordingly, the healthcare worker can confirm changes in the condition of each patient from locations other than the nurse station.

[Configuration of Station Server]

Figure 2:
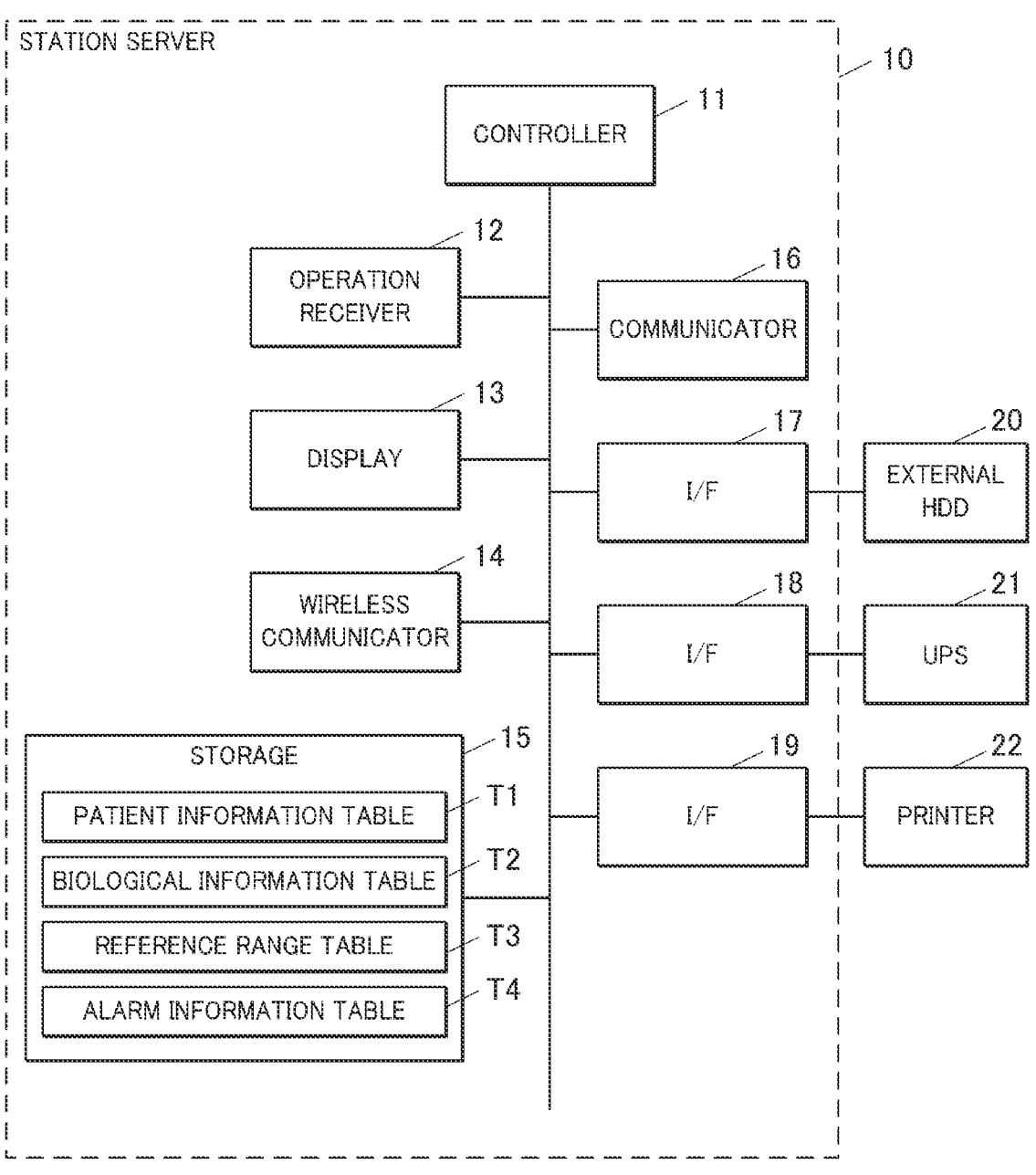
FIG. 2 is a block diagram showing a functional configuration of a station server.

FIG. 2 is a block diagram showing a functional configuration of the station server 10.

As shown in FIG. 2, the station server 10 includes a controller 11, an operation receiver 12, a display 13, a wireless communicator 14, a storage 15, a communicator 16, and interfaces (I/Fs) 17 to 19, which are connected via a bus.

The controller 11 includes a central processing unit (CPU), and a random access memory (RAM), and comprehensively controls processing operation of the components of the station server 10. Specifically, the CPU reads various processing programs stored in the storage 15, loads the programs into the RAM, and performs various processes in cooperation with the programs.

The operation receiver 12 includes a keyboard including cursor keys, character and numeric input keys, and various function keys, and a pointing device, such as a mouse, and outputs an operation signal input through key operation on the keyboard, and mouse operation, to the controller 11.

The display 13 includes a monitor, such as a liquid crystal display (LCD), and displays various screens in accordance with an instruction of a display signal input from the controller 11.

The wireless communicator 14 is a wireless interface for transmitting and receiving data to and from the bedside terminal 30 and the mobile terminal 60 through wireless communication.

The storage 15 includes an HDD, or a nonvolatile semiconductor memory, and stores various data items. The storage 15 stores a patient information table T1, a biological information table T2, a reference range table T3, an alarm information table T4, etc.

The patient information table T1 associates patient information with each patient. The patient information includes a patient ID, a patient name, a gender, birth date, a room number, and a bed number. The patient information is stored in the patient information table T1 through preliminary input, or obtainment of information on an electronic health record from external equipment.

The biological information table T2 associates the biological information with respect to each patient, and with each type (item) of the biological information. The biological information is time-series data continuously obtained through each bedside terminal 30. The biological information may include the respiratory rate, $SpO_2$, pulse rate, heart rate, $V_E$, etc. The biological information table T2 stores the patient ID of the target patient, the type (item) of biological information, the measurement date and time, and a measured value in association with each other.

The reference range table T3 stores the reference range with respect to each patient and to each type (item) of the biological information, in association with each other. The reference range is a range for the biological information determined to be normal. An upper limit value, and a lower limit value, or only one of these values is set in the reference range. The reference range is set by a doctor, or a nurse under guidance by a doctor in consideration of each patient's age, gender, current medical condition, and past medical history, on a patient-by-patient basis.

The alarm information table T4 stores the patient ID of the target patient, alarm occurrence date and time, alarm content, clearance date and time, and the like in association with each other.

The communicator 16 is made up of a network interface or the like, and transmits and receives data to and from an external apparatus connected via communication networks, such as a local area network (LAN), a wide area network (WAN), and the Internet.

The I/Fs 17 to 19 are interfaces for connection to various external apparatuses. Here, the I/Fs 17 to 19 are each connected to the external HDD 20, the UPS 21, and the printer 22.

The controller 11 causes the display 13 to display biological information on a plurality of patients serving as monitoring targets. Specifically, the controller 11 displays graphs and the like indicating measured values (numerical values) of and temporal change in the biological information on the patients. The temporal change is change along the time of the biological information, and is, for example, change in representative values (mean, median, mode, maximum, minimum, etc.) of the biological information in a freely selected time period.

The controller 11 determines whether the biological information on the processing target patient has an abnormality or not. For example, the controller 11 obtains the reference range of the target item of the processing target patient from the reference range table T3 in the storage 15, and determines that an abnormality is present if the biological information on the processing target patient includes a value out of the reference range. Even if the bedside terminal 30 associated with the processing target patient causes an abnormality in data obtainment from the biological information detector 40 (see FIG. 3), or data communication with the station server 10, the controller 11 determines that an abnormality is present.

If the biological information on the processing target patient includes an abnormality, the controller 11 generates alarm information, and causes the storage 15 to store the generated alarm information. Specifically, the controller 11 stores the patient ID of the patient about which an alarm occurs, the alarm occurrence date and time, the alarm content and the like in association with each other in the alarm information table T4. If the biological information on the processing target patient includes an abnormality, the controller 11 changes the background color of the measured value to be displayed on the display 13 to a color different from that in a surrounding area, thus issuing a notification about alarm.

Note that when the alarm is cleared, the controller 11 stores the clearance date and time in association with the patient ID concerned, the alarm occurrence date and time, and the alarm content, in the alarm information table T4 in the storage 15.

[Configuration of Bedside Terminal]

Figure 3:
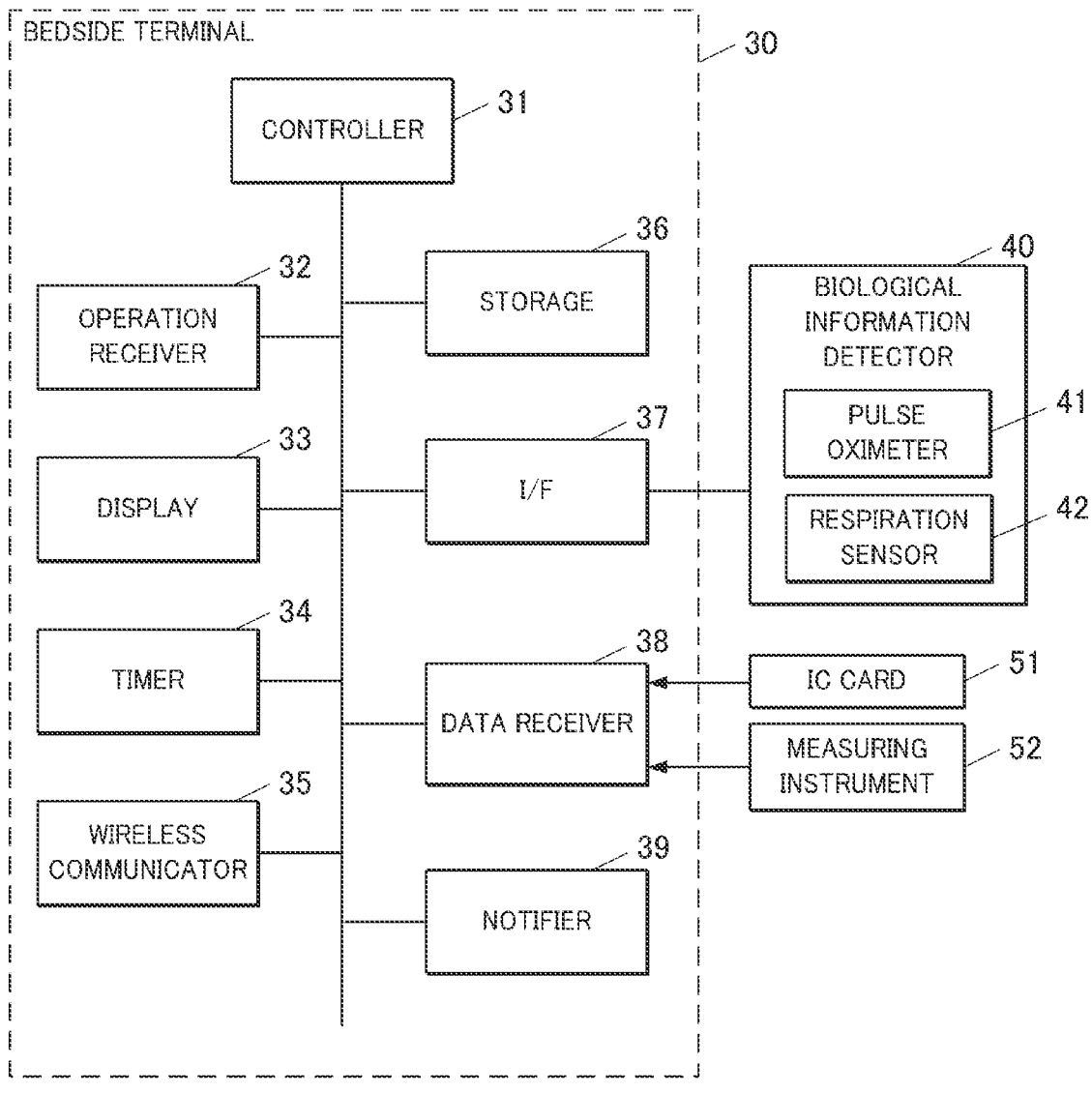
FIG. 3 is a block diagram showing a functional configuration of a bedside terminal.

FIG. 3 shows a functional configuration of the bedside terminal 30.

As shown in FIG. 3, the bedside terminal 30 includes a controller 31 (hardware processor), an operation receiver 32, a display 33, a timer 34, a wireless communicator 35, a storage 36, an interface (I/F) 37, a data receiver 38, and a notifier 39, which are connected via a bus.

The controller 31 includes a CPU, and a RAM, and comprehensively controls processing operations of the components of the bedside terminal 30. Specifically, the CPU reads various processing programs stored in the storage 36, loads the programs into the RAM, and performs various processes in cooperation with the programs.

The operation receiver 32 includes various switches, and various functional buttons, and outputs operation signals of these components to the controller 31. The operation receiver 32 is made up of a touch panel stacked on the display 33, accepts an input by the user onto the display screen, and outputs an operation signal in accordance with the position of the touch operation to the controller 31.

The display 33 includes an LCD, and displays various screens in accordance with an instruction of a display signal input from the controller 31. For example, the display 33 displays biological information obtained from the pulse oximeter 41, and the respiration sensor 42.

The timer 34 includes a timer circuit (RTC: Real Time Clock), measures the current date and time by the timer circuit, and outputs the date and time to the controller 31.

The wireless communicator 35 is a wireless interface for transmitting and receiving data to and from the station server 10 and the mobile terminal 60 through wireless communication.

The storage 36 includes a nonvolatile semiconductor memory, and stores various processing programs, parameters, and files and the like required to execute the programs. The storage 36 stores the biological information on the patient associated with the bedside terminal 30. The storage 36 also stores the patient information on the patient associated with the bedside terminal 30, and a threshold used to determine the reliability degree of the biological information.

The I/F 37 obtains the biological information on the patient, from the biological information detector 40, which includes the pulse oximeter 41 and the respiration sensor 42 connected via cables.

The data receiver 38 is made up of a NFC reader. The data receiver 38 obtains identification information on a healthcare worker from the IC card 51 owned by the healthcare worker. The data receiver 38 obtains the biological information on the patient from the measuring instrument 52 that supports the NFC. For example, the information obtained from the data receiver 38 is associated with the current date and time obtained from the timer 34, and stored in the storage 36.

The notifier 39 includes a light emitting diode (LED), and a speaker. The notifier 39 turns on the LED, and issues a beep from the speaker in accordance with control by the controller 31, thus issuing a notification to the user.

The controller 31 obtains the biological information on the patient. That is, the controller 31 functions as an obtainer.

The controller 31 continuously obtains, through the I/F 37, measurement data of biological information on the patient, from the biological information detector 40, which includes the pulse oximeter 41, and the respiration sensor 42. For example, the controller 31 obtains measurement data including $SpO_2$, and the pulse rate from the pulse oximeter 41, and obtains measurement data including the respiratory waveform, and the respiratory rate from the respiration sensor 42. The controller 31 causes the storage 36 to store the measured value of the biological information, and the measurement date and time of the measured value (the current date and time obtained from the timer 34) in association with each other, with respect to each type (item) of the biological information.

Specifically, the respiration sensor 42 measures body motions including the biological information, and generates a body motion signal.

The controller 31 reads the body motion signal from the respiration sensor 42, and obtains parameters pertaining to signals of the received power and the pressure (in the case of the piezoelectric sensor) obtained with the body motion signal.

The controller 31 extracts a respiration signal from the body motion signal. The controller 31 calculates the respiratory rate, its statistics (variance, variation coefficient, etc.) and the like, based on the respiration signal.

Note that biomedical sensors used by the bedside terminal 30 are not limited to the respiration sensor 42, and may include what measures the body motions including information on heartbeats, and generates the body motion signal. In this case, the controller 31 extracts a heartbeat signal from the body motion signal, calculates the heart rate, its statistics (variance, variation coefficient, etc.) and the like, based on the heartbeat signal.

The controller 31 causes the display 33 to display a time-series graph of the measured value (real-time numerical value), waveforms and the like of the biological information on the patient obtained from the biological information detector 40 through the I/F 37.

The controller 31 associates the type (item) of the biological information on the patient, the measured values, and the measurement date and time obtained from the biological information detector 40, with the patient ID of this patient, and transmits them to the station server 10 through the wireless communicator 35.

The controller 31 determines the reliability degree of the biological information. That is, the controller 31 functions as a reliability degree determiner.

The reliability degree is an indicator for determining the reliability of the biological information. Here, not only the reliability degree representing the reliability as the magnitude of the numerical value (for instance, the reliability is high because the reliability degree is 90%), but also an indicator itself contributing to the reliability degree may sometimes be regarded as the reliability degree.

For example, the controller 31 compares the received power when receiving the biological information, the magnitude of phase variation, the statistics of the measured values and the like, respectively with thresholds, and determines the reliability degree of the biological information. The thresholds are preliminarily stored in the storage 36, and can be appropriately changed in accordance with an instruction from the station server 10.

The controller 31 derives the reason of the determination result of the reliability degree of the biological information. That is, the controller 31 functions as a reason deriver.

The controller 31 causes the display 33 to display information related to the reason of the determination result of the reliability degree. That is, the controller 31 functions as a display controller. The "information related to the reason of the determination result" may be the reason of the determination result, or information allowing the reason of the determination result to be recognized.

The reason of the determination result is a reason caused by the living body of the patient, or a reason caused by what is other than the living body of the patient. What is other than the living body of the patient includes, for example, an apparatus related to measurement, such as the biological information detector 40, a communication environment and the like.

The controller 31 causes the display 33 to display information related to the reason of the determination result, in a display mode in accordance with the reason of the determination result. For example, the controller 31 achieves suitable display content in accordance with the reason of each determination result, and adds different colors.

The number of reasons of the determination result of the reliability degree of the biological information is one in some cases, or more than one in the other cases.

If the reason of the determination result of the reliability degree of the biological information includes at least a first reason and a second reason, the controller 31 displays information related to the first reason, and information related to the second reason, on the same screen of the display 33.

Furthermore, the controller 31 may cause the display 33 to display the reliability degree.

If it is determined that the reliability degree is lower than a predetermined reference by determination of the reliability degree, the controller 31 causes the display 33 to display information related to the reason of the low reliability degree. Hereinafter, a fact that the reliability degree is lower than the predetermined reference is sometimes simply represented: "the reliability degree is low", and a fact that the reliability degree is equal to or higher than the predetermined reference is sometimes simply represented: "the reliability degree is high".

If it is determined that the reliability degree is lower than a predetermined reference by determination of the reliability degree, the controller 31 causes the display 33 to display measures against the reason of the low reliability degree. For example, the controller 31 causes the display 33 to display measures including "Keep radio wave sensor away from patient", and "Remove obstacle". The user takes measures including adjustment of the position of the respiration sensor 42 (radio wave sensor), and reviewing of the installation environment.

If it is determined that the reliability degree is lower than the predetermined reference by determination of the reliability degree, the controller 31 causes the display mode on the display 33 to be a display mode different from a mode before determination of the reliability degree to be lower than the predetermined reference. For example, the controller 31 causes part or the entirety of the display screen including the biological information to be in a display mode different from the mode before determination of the reliability degree to be low, or to be in a display mode different from the mode before determination of the reliability degree to be low, by blinking an area out of the screen.

If it is determined that the reliability degree is lower than the predetermined reference by determination of the reliability degree, the controller 31 controls the notifier 39 to issue a notification about the determination result. For example, the notifier 39 turns on the LED, and issues a beep from the speaker, thus issuing a notification about the determination result that the reliability degree is low. If it is determined that the reliability degree is lower than a predetermined reference by determination of the reliability degree, the controller 31 causes the display 33 to display the determination result that the reliability degree is low.

FIG. 4 shows a classification example of reasons of low reliability degrees. In FIG. 4, each reason of the low reliability degree is associated with an occurring event, an adverse effect, a display method, and measures.

The occurring event is an event caused by "REASON OF LOW RELIABILITY DEGREE", or an event serving as a cause of reduction in reliability degree.

The adverse effect is an adverse effect caused by "REASON OF LOW RELIABILITY DEGREE".

The display method is information indicating how the user is notified of "REASON OF LOW RELIABILITY DEGREE".

The measures are measures that the user should take against "REASON OF LOW RELIABILITY DEGREE".

"EXCESSIVE INPUT DISPLAY" shown in "DISPLAY METHOD" in FIG. 4 is a display method indicating that the input (a received signal for obtaining biological information) is too high.

"TOO LOW INPUT DISPLAY" is a display method indicating that the input (the received signal for obtaining biological information) is too low.

"ANTENNA DISPLAY" is a display method indicating the intensity of the received signal for obtaining biological information by means of the number of antennas.

"BED LEAVING DISPLAY" is a display method indicating that the patient is away from the bed.

"INFREQUENT RESPIRATION/APNEIC DISPLAY" is a display method indicating that the patient is in an infrequent respiration/apneic state.

"BRADYPNEA/TACHYPNEA DISPLAY" is a display method indicating that the patient is in a bradypnea/tachypnea state.

"MEASURED VALUE TIME-SERIES DISPLAY" is a display method indicating temporal variation in measured values, such as a graph of the time-series data of the measured values along a lapse of time.

"SPECTRUM DISPLAY" is a display method of a graph (spectrum) indicating the distribution of signal intensities where signal values are resolved with respect to each frequency (wavelength).

"HISTOGRAM DISPLAY" is a display method indicating the frequency in each interval when the measured values are divided in multiple intervals, in a graph (histogram).

"STATISTICS DISPLAY" is a display method indicating the standard deviation, variation coefficient and the like of the measured values.

"MEASUREMENT CANDIDATE TWO-DIMENSIONAL DISPLAY" is a display method indicating the positions of measurement candidates detected by the radio wave sensor (respiration sensor 42) on a two-dimensional plane (map).

"BODY MOTION DISPLAY" is a display method indicating that the patient has a body motion.

FIG. 4 also shows whether there is a possibility that the reason of the low reliability degree is caused by the living body or not (circle/cross mark), and caused by what is other than the living body or not (circle/cross mark). For example, the excessive or too low received signal, and the excessive or too low measured value are caused by the living body in some cases, and caused by what is other than the living body. On the other hand, the too small phase variation in received signal, the large variation in measured value, presence of multiple measurement candidates, and effects on measured values due to a body motion are caused by the living body.

[Configuration of Mobile Terminal]

Figure 5:
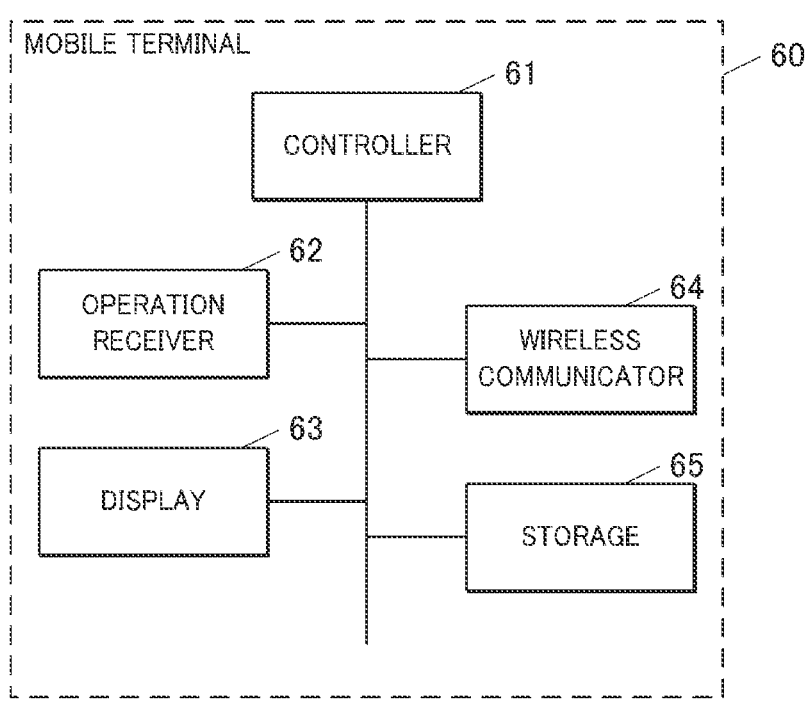
FIG. 5 is a block diagram showing a functional configuration of a mobile terminal.

FIG. 5 illustrates a functional configuration of the mobile terminal 60.

As illustrated in FIG. 5, the mobile terminal 60 includes a controller 61, an operation receiver 62, a display 63, a wireless communicator 64, and a storage 65, which are connected via a bus.

The controller 61 includes a CPU, and a RAM, and comprehensively controls processing operation of the components of the mobile terminal 60. Specifically, the CPU reads various processing programs stored in the storage 65, loads the programs into the RAM, and performs various processes in cooperation with the programs.

The operation receiver 62 includes various function keys, and a touch panel stacked on the display 63, and outputs an operation signal in accordance with a key operation, and the position of the touch operation, to the controller 61.

The display 63 includes a monitor, such as of an LCD, and displays various screens in accordance with an instruction of a display signal input from the controller 61.

The wireless communicator 64 is a wireless interface for transmitting and receiving data to and from the station server 10 and the bedside terminal 30.

The storage 65 includes a nonvolatile semiconductor memory, and stores various processing programs, parameters, and files and the like required to execute the programs.

[Operation of Bedside Terminal]

Next, operation in the bedside terminal 30 is described.

FIG. 6 is a flowchart showing a reliability degree determination reason display process executed by the bedside terminal 30. This process is achieved by a software process through cooperation between the CPU of the controller 31, and the programs stored in the storage 36.

First, the controller 31 obtains the biological information on the patient associated with the bedside terminal 30 (the respiratory rate, SpO$_2$, pulse rate, etc.) from the biological information detector 40 (the pulse oximeter 41, and the respiration sensor 42) via the I/F 37 (Step S1).

The controller 31 accumulates, in the storage 36, the biological information measurement data obtained from the biological information detector 40 (Step S2). The controller 31 causes the storage 36 to store the measured value of the biological information, and the measurement date and time of the measured value in association with each other, with respect to each type of the biological information.

Next, the controller 31 sets one of indicators used to determine the reliability degree of the biological information as a processing target (Step S3).

Next, the controller 31 calculates the statistics of the biological information, with respect to the processing target indicator (Step S4). Here, use of the statistics having certain characteristics depends on which reference (indicator) is used to determine the reliability degree.

Next, the controller 31 compares the calculated statistics with the threshold associated with the processing target indicator, and determines the reliability degree, based on the comparison result (Step S5). Here, the basis for determining the reliability degree is a reason of the determination result.

That is, the controller 31 derives the reason of the determination result of the reliability degree of the biological information.

Next, the controller 31 causes the storage 36 to store the determination result of the reliability degree with respect to the processing target indicator (Step S6). Specifically, the controller 31 causes the storage 36 to store the processing target indicator, the determination result of whether the reliability degree of the biological information is low or not based on comparison with the predetermined reference, and the reason of the determination result, in association with each other.

Here, the controller 31 determines whether the processing has been finished for each predefined indicator or not (Step S7).

If the indicator for which the processing has not been finished yet (Step S7: NO), the processing returns to Step S3, and the processing is repeated for another indicator.

If it is determined that the processing has been finished for each indicator in step S7 (Step S7: YES), the controller 31 determines whether there is any indicator having a low reliability degree or not (Step S8).

If there is any indicator having a low reliability degree (Step S8: YES), the controller 31 causes the display 33 to display information related to the reason of the low reliability degree with respect to the indicator (Step S9). The controller 31 may display the reason itself of the low reliability degree, or display information allowing the low reliability to be recognized (determined).

Here, the controller 31 causes the display 33 to display the information related to the reason of the low reliability degree, in a display mode in accordance with the reason of the determination result. For example, the controller 31 achieves display contents suitable for the respective reasons, with respect to each of the reasons of the determination results, thus achieving display modes different from each other. The controller 31 changes the colors of information related to the reason of the low reliability degree, depending on each of the reasons of the determination results, thus achieving the display modes different from each other.

If the reliability degree is determined to be low, the controller 31 causes the display 33 to display the entirety of the display screen (biological information display screen etc.) or part of this display screen (in particular, a site associated with the reason of the low reliability degree etc.) displayed on the display 33, in a display mode different from the mode before determination of the reliability degree to be low. For example, the controller 31 displays the entirety or part of the display screen in a blinking manner. Alternatively, if the reliability degree is determined to be low, the controller 31 may cause the display mode in an area out of the display screen (biological information display screen etc.) displayed on the display 33 to be different from the mode before determination of the reliability degree to be low.

Furthermore, the controller 31 may control the notifier 39, and issue a notification about a determination result that the reliability degree is low, through lighting of the LED, a beep, etc.

For the indicator having a low reliability degree, the controller 31 causes the display 33 to display measures against the reason of the low reliability degree (Step S10).

After Step S10, if there is not any indicator having a low reliability degree in Step S8 (Step S8: NO), the controller 31 causes the display 33 to display required statistics (measured values etc.) (Step S11).

Thus, the reliability degree determination reason display process is finished.

FIG. 7 shows an example of a display method of a condition of determining "reliability degree is high", a condition of determining "reliability degree is low", and the case with a low reliability degree, with respect to each indicator used to determine the reliability degree. Based on the indicator suitable for an event where the example described here occurs, the measurement situations (reliability degree) of the biological information is determined, which allows the user to recognize the measurement situations of the biological information in details, and take appropriate measures.

Note that the reliability degree determination reason display process (see FIG. 6) determines the reliability degree with respect to each indicator. Alternatively, it may be determined whether the reliability degree is lower than the predetermined reference or not based on multiple indicators.

The reliability degree determination reason display process (see FIG. 6) repeats determination of the reliability degree for the indicator on an indicator-by-indicator basis. For facilitating understanding, pieces of processing (a first specific example, and a second specific example) for a certain indicator are picked up from the reliability degree determination reason display process, and are described.

Figure 8:
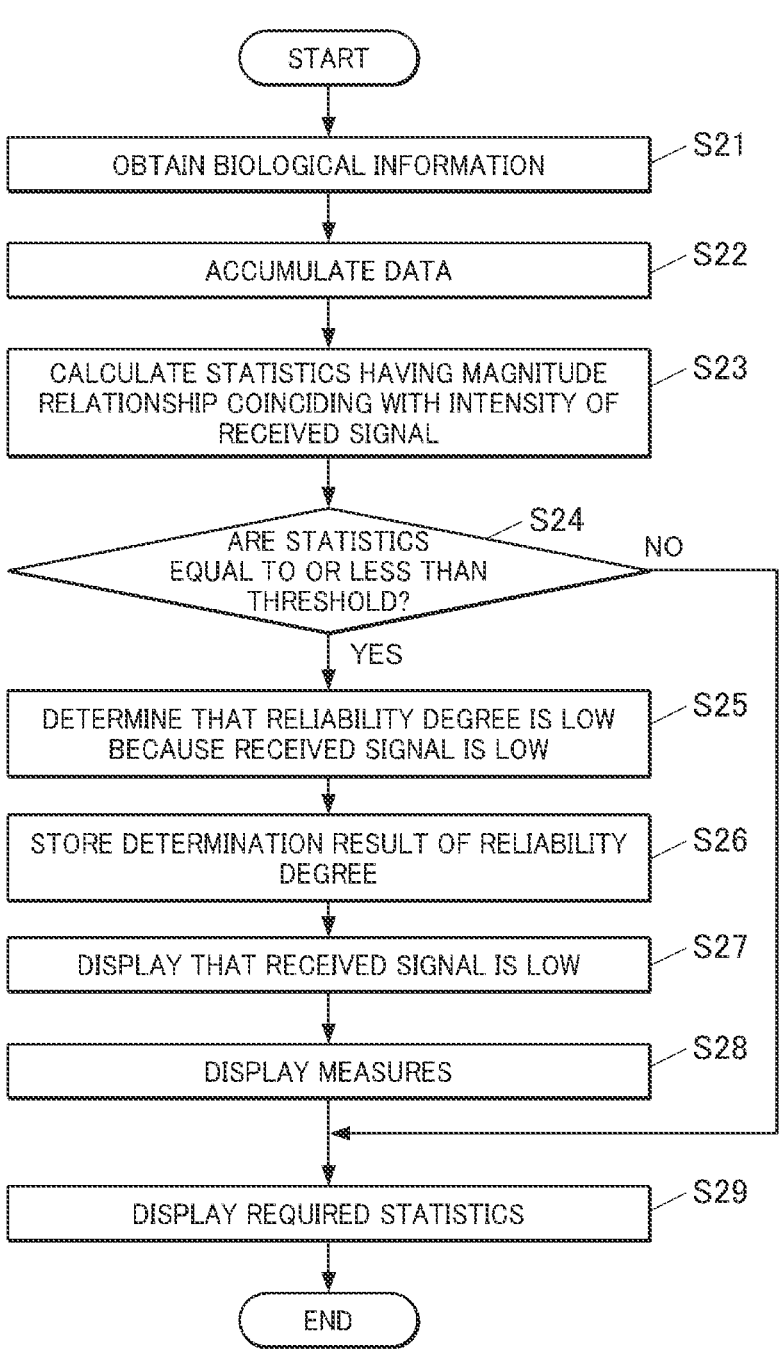
FIG. 8 is a flowchart showing a case (first specific example) where a radio wave received signal of a respiration sensor is too low.

Referring to FIG. 8, a case is described where a radio wave sensor is selected as the respiration sensor 42 (biomedical sensor), and the radio wave received signal is too low with respect to the reception performance of the respiration sensor 42 (first specific example). In this embodiment, the fact that the received signal is lower than a predetermined reference is sometimes represented simply as "the received signal is low".

The processes of Steps S21 and S22 are similar to the processes of Steps S1 and S2 in the reliability degree determination reason display process (see FIG. 6). Accordingly, the description is omitted.

Next, the controller 31 calculates the statistics having the magnitude relationship coinciding with the intensity of the received signal, from the received signal of the respiration sensor 42 (Step S23). For example, the instantaneous value of the received power of the received signal, its mean, and the like are used as the statistics having the magnitude relationship coinciding with the intensity of the received signal.

Next, the controller 31 compares the calculated statistics with a predetermined threshold, and determines whether the statistics are equal to or less than the threshold or not (Step S24). The threshold is a value serving as a boundary for determining whether or not the intensity of the received signal is a sufficient intensity for allowing the respiration sensor 42 (radio wave sensor) to achieve a desired performance.

If the statistics are equal to or lower than the threshold (Step S24: YES), i.e., if the intensity of the received signal is insufficient for allowing the respiration sensor 42 to achieve the desired performance, the controller 31 determines that the reliability degree of the respiratory rate is low because the received signal is low (Step S25).

Next, the controller 31 causes the storage 36 to store the determination result of the reliability degree (Step S26).

Next, the controller 31 causes the display 33 to display that the received signal is low (Step S27). Here, the fact that the received signal is low corresponds to information related to the reason of the low reliability degree of the respiratory rate.

The controller 31 causes the display 33 to display measures against the fact that the received signal is low (Step S28). For example, the controller 31 displays "Bring respiration sensor close to person", "Remove obstacle" and the like.

After Step S28, or if the statistics are determined to be higher than the threshold in Step S24 (Step S24: NO), the controller 31 causes the display 33 to display required statistics (Step S29). For example, the controller 31 causes the display 33 to display the measurement result (the measured value of the respiratory rate etc.) obtained from the received signal.

The first specific example is thus finished.

In the first specific example, if the statistics is equal to or lower than the threshold, the reliability degree is determined to be low. Alternatively, the reliability degree may be determined to be low if the statistics are lower than the threshold.

By confirming the display that "the received signal is low", and the measures, the user can take measures: "the respiration sensor is installed close to a person", "the obstacle as a cause of power propagation loss is removed" and the like.

Note that the display "the received signal is low" may be an antenna display used for mobile phones and the like, and display by characters, etc. However, there is no limitation to them.

Figure 9A:
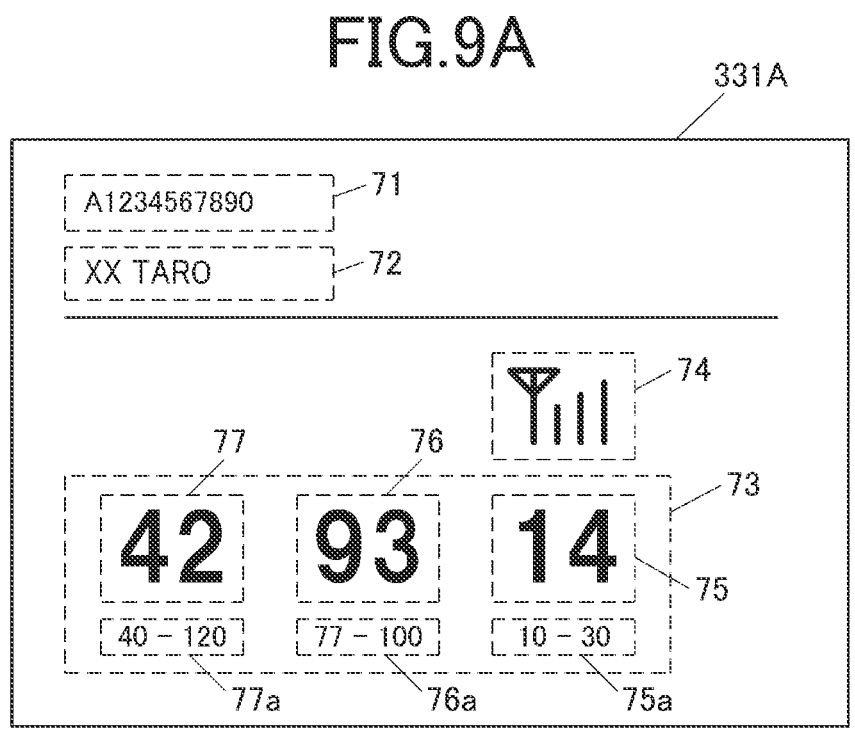
FIG. 9A shows an example of a biological information display screen including the quality of the received signal (antenna display)
Figure 9B:
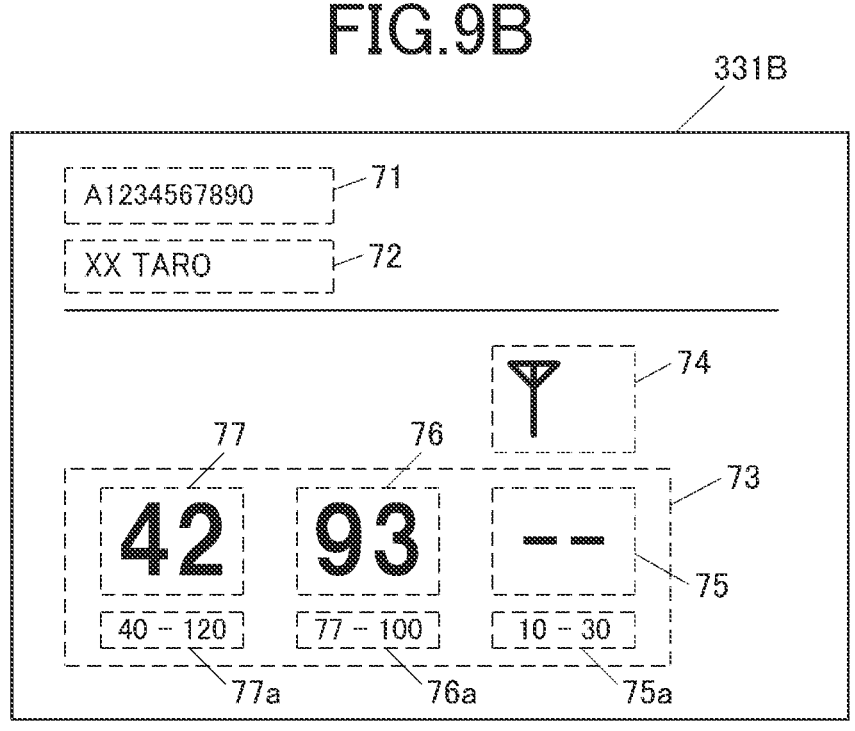
FIG. 9B shows an example of a biological information display screen including the quality of the received signal (antenna display)
Figure 9C:
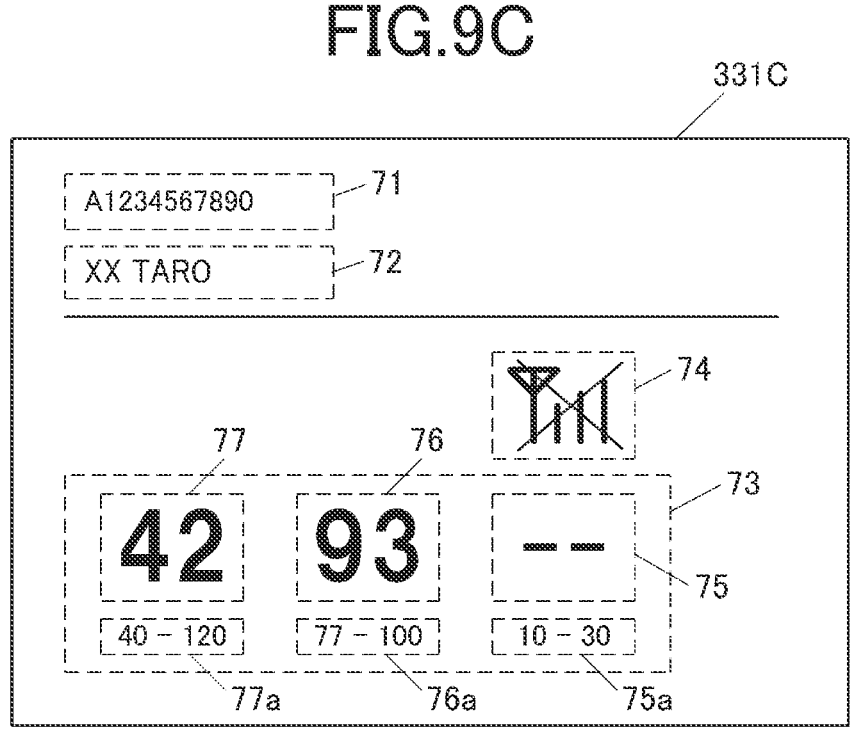
FIG. 9C shows an example of a biological information display screen including the quality of the received signal (antenna display)

FIGS. 9A, 9B and 9C show examples of biological information display screens 331A, 331B, and 331C that include the quality (antenna display) of the received signal, and are displayed on the display 33. The biological information display screens 331A, 331B, and 331C include a patient ID display area 71, a patient name display area 72, a measured value display area 73, and a signal quality display area 74.

The patient ID of a target patient is displayed in the patient ID display area 71.

The patient name of the target patient is displayed in the patient name display area 72.

The measured values (numerical values) of the biological information are displayed in the measured value display area 73. The measured value display area 73 includes a respiratory rate display area 75, an $SpO_2$ display area 76, and a pulse rate display area 77. The latest (current) values of the respiratory rate, $SpO_2$, and pulse rate are displayed respectively in the respiratory rate display area 75, the $SpO_2$ display area 76, and the pulse rate display area 77. Note that pieces of the biological information determined to have a reliability degree lower than the predetermined reference are displayed as blank fields, such as "--", in the respiratory rate display area 75, the $SpO_2$ display area 76, and the pulse rate display area 77, without any measured value display.

Respectively below the respiratory rate display area 75, the $SpO_2$ display area 76, and the pulse rate display area 77, there are arranged reference range display areas 75a, 76a, and 77a. Reference ranges (normal ranges) of items for the target patient are respectively indicated in the reference range display areas 75a, 76a, and 77a. As for the reference ranges, the information stored in the reference range table T3 in the storage 15 is obtained from the station server 10, and stored in the storage 36.

In the signal quality display area 74, the intensity of the received signal of the respiration sensor 42 (radio wave sensor) is displayed as the signal quality in a four-staged manner (the number of antennas: 0, 1, 2, or 3). Note that the signal intensity of the radio wave sensor depends not only simply on the received power but also on the displacement of the measurement target. Accordingly, it is preferable to evaluate the signal quality in view of the S/N ratio.

The biological information display screen 331A shown in FIG. 9A is an example in a case where the signal quality is favorable. A state is displayed where three antennas are shown in the signal quality display area 74. On the biological information display screen 331A, the content displayed in the signal quality display area 74 is a reason that the reliability degree of the respiratory rate is high (favorable signal quality), and is also the reliability degree itself (signal level: 3).

The biological information display screen 331B shown in FIG. 9B is an example where the signal quality is unfavorable (a case where the received signal is too low). A state is displayed where no antenna is shown in the signal quality display area 74. On the biological information display screen 331B, the content displayed in the signal quality display area 74 is a reason that the reliability degree of the respiratory rate is low (the received signal is too low), and is also the reliability degree itself (signal level: 0). Due to the unfavorable signal quality of the respiration sensor 42, the reliability degree of the respiratory rate decreases. Accordingly, the respiratory rate display area 75 on the biological information display screen 331B is blank.

The biological information display screen 331C shown in FIG. 9C is an example where the signal quality is unfavorable (a case where the received signal is too high), and x (a cross mark) is displayed over the state with three antennas standing in the signal quality display area 74. On the biological information display screen 331C, the content displayed in the signal quality display area 74 is a reason that the reliability degree of the respiratory rate is low (the received signal is too high), and is also the reliability degree itself (unworthy of reliability). Due to the unfavorable signal quality of the respiration sensor 42, the reliability degree of the respiratory rate decreases. Accordingly, the respiratory rate display area 75 on the biological information display screen 331C is blank.

Figure 10:
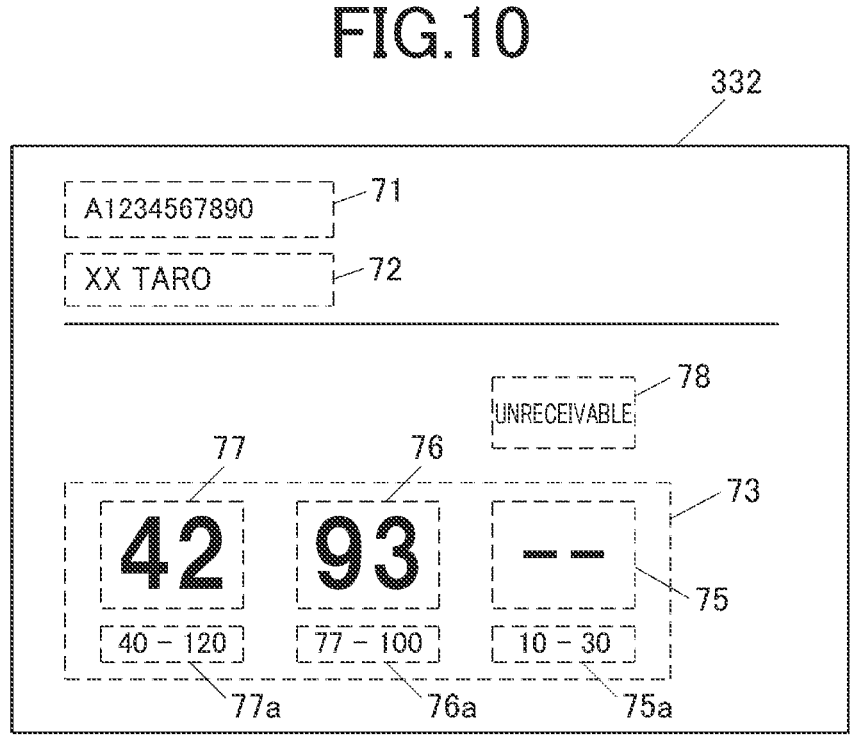
FIG. 10 shows an example of a biological information display screen including the quality of the received signal (character display)

FIG. 10 shows an example of a biological information display screen 332 including the quality of the received signal (character display) displayed on the display 33. On the biological information display screen 332, components similar to those on the biological information display screen 331B (see FIG. 9B) are assigned the identical symbols, and the description is omitted. The biological information display screen 332 includes a signal quality display area 78.

In a case where the reliability degree of the respiratory rate is low, characters "UNRECEIVABLE" are indicated as the signal quality in the signal quality display area 78. The content displayed in the signal quality display area 78 is a reason of the low reliability degree of the respiratory rate (incapable of receiving the signal, and the received signal is too low).

With the display of the signal quality as described above, measures against the problem of disturbing measurement may also be displayed.

Figure 11:
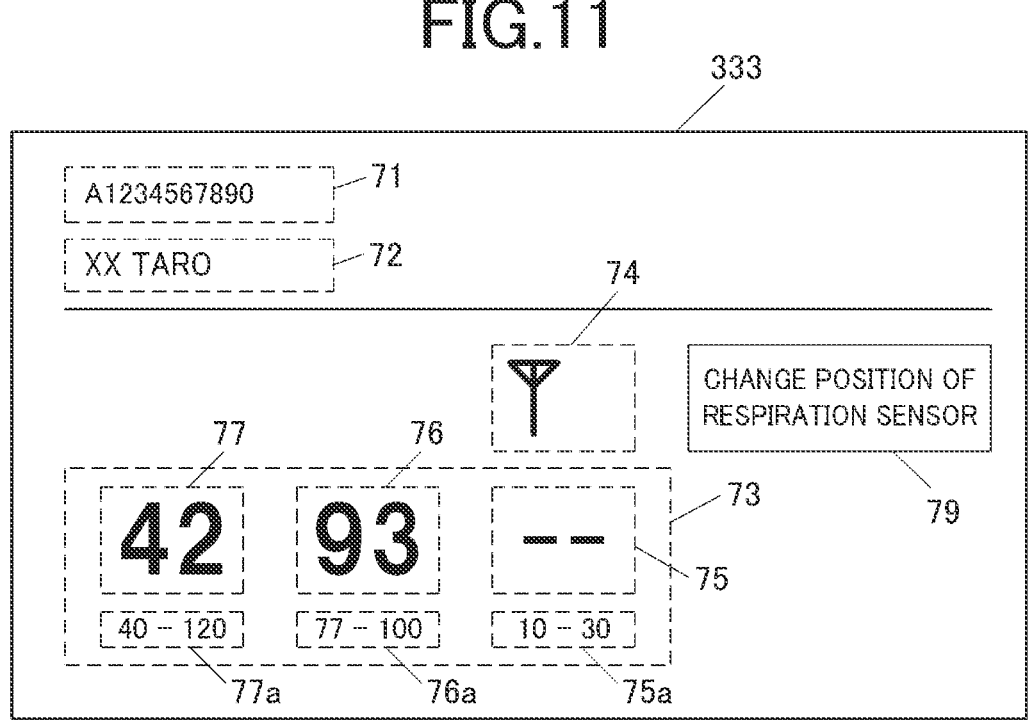
FIG. 11 shows an example of a biological information display screen including the quality of the received signal (antenna display), and measures.

FIG. 11 shows an example of a biological information display screen 333 including the quality of the received signal (antenna display), and measures that are displayed on the display 33. On the biological information display screen 333, components similar to those on the biological information display screen 331B (see FIG. 9B) are assigned the identical symbols, and the description is omitted. The biological information display screen 333 includes a measures display area 79.

In the measures display area 79, a message "CHANGE POSITION OF RESPIRATION SENSOR" is displayed as measures associated with the reason of the low reliability degree of the respiratory rate (an antenna display displaying that the received signal is too low, in the signal quality display area 74).

Other examples of measures associated with "unfavorable signal quality" include "Remove object as impediment concerning propagation loss", and "Reduce distance between respiration sensor and measurement target".

Figure 12:
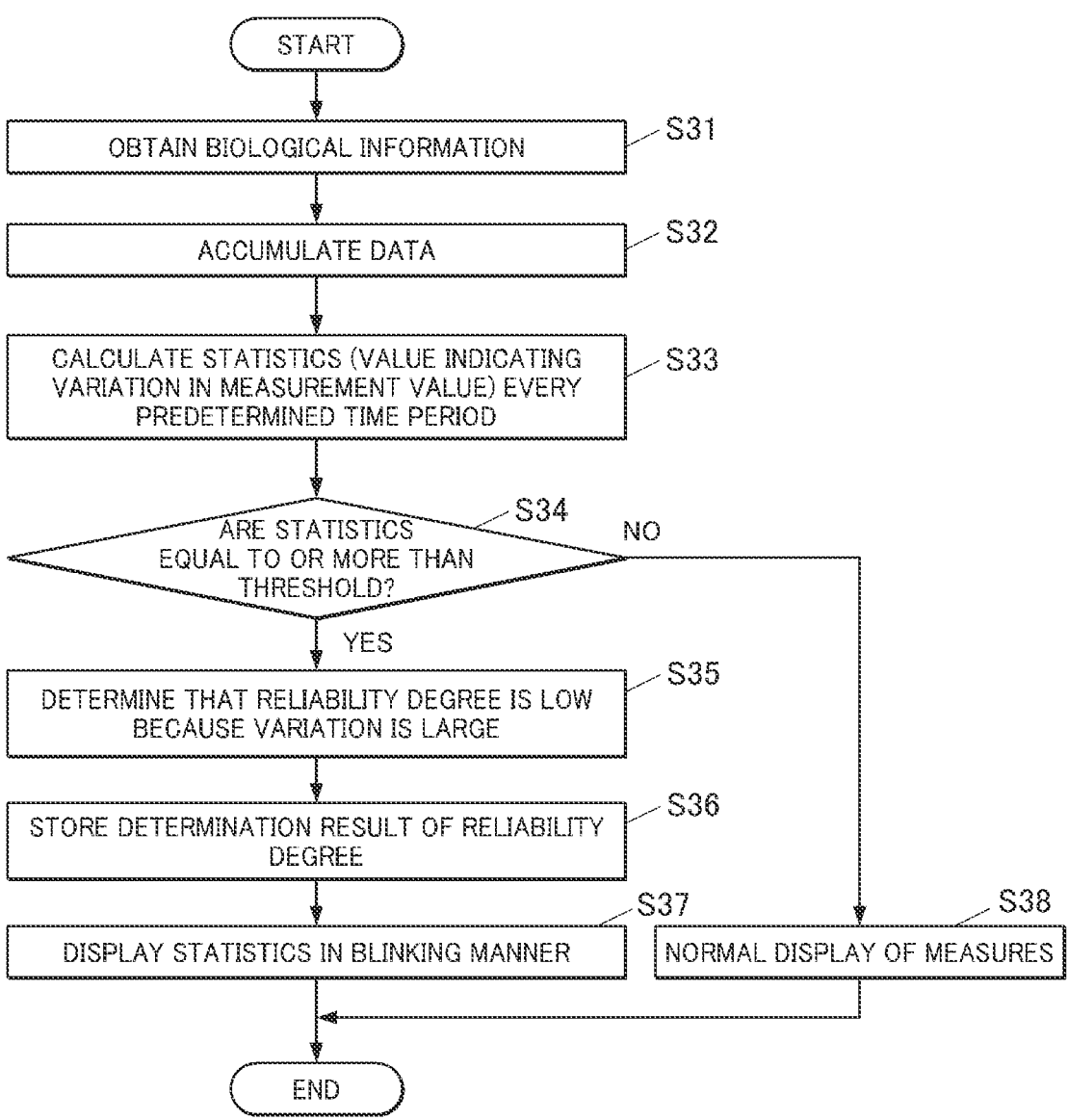
FIG. 12 is a flowchart showing a case (second specific example) where the variation in measured value is large.

Next, referring to FIG. 12, a case with a large variation in measured value (second specific example) is described. In this embodiment, the fact that the variation is larger than the predetermined reference is sometimes represented simply: "the variation is high".

The processes of Steps S31 and S32 are similar to the processes of Steps S1 and S2 in the reliability degree determination reason display process (see FIG. 6). Accordingly, the description is omitted.

Next, the controller 31 calculates the statistics (a value indicating variation in measured value) from the biological information (or the received signal) every constant time period (Step S33). The sample standard deviation, sample variance, and the like are typically used as the statistics indicating the variation. Alternatively, the difference between the mean and the minimum, the difference between the mean and the maximum, the difference between the minimum and the maximum, and the like may be adopted.

Next, the controller 31 compares the calculated statistics with a predetermined threshold, and determines whether the statistics are equal to or higher than the threshold or not (Step S34). The threshold is a value serving as a boundary for determining whether the variation in measured value is in a reliable range or not.

If the statistics are equal to or higher than the threshold (Step S34: YES), the controller 31 determines that the reliability degree of the biological information is low because the variation is large (Step S35).

Next, the controller 31 causes the storage 36 to store the determination result of the reliability degree (Step S36).

Next, the controller 31 causes the display 33 to display the statistics (the value indicating the variation in measured value) in a blinking manner (Step S37). Here, the blinking display of the statistics corresponds to display of the information related to the reason of the low reliability degree of biological information.

If the statistics are determined to be less than the threshold in Step S34 (Step S34: NO), the controller 31 causes the display 33 to display statistics as normal display (Step S38).

After Step S37 or S38, the second specific example is finished.

In the second specific example, if the statistics is equal to or higher than the threshold, the reliability degree is determined to be low. Alternatively, the reliability degree may be determined to be low if the statistics are higher than the threshold.

Figures 13A, 13B:
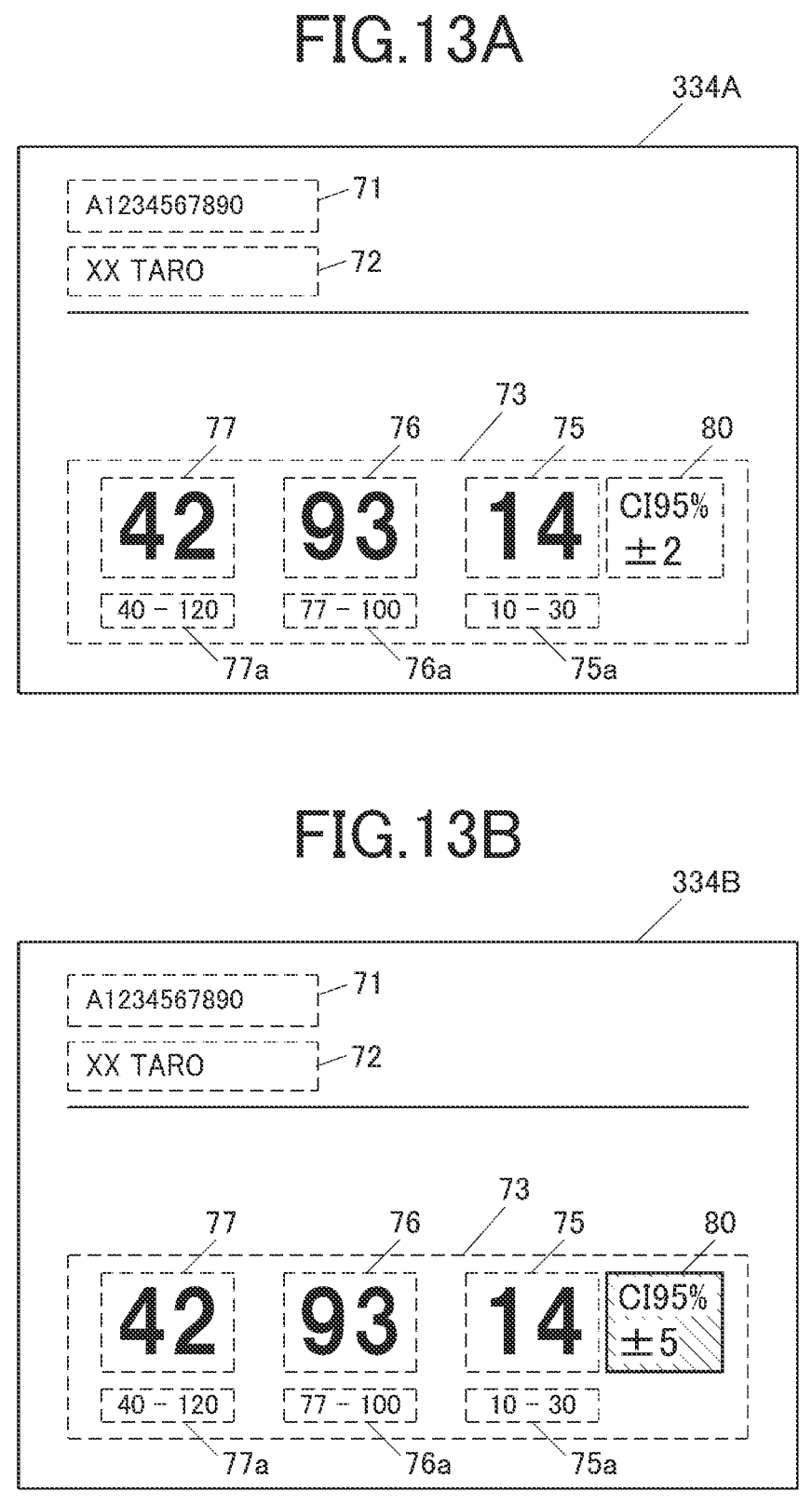

FIGS. 13A and 13B show examples of biological information display screens 334A and 334B that include the variation, and are displayed on the display 33. On the biological information display screens 334A and 334B, components similar to those on the biological information display screen 331A (see FIG. 9A) are assigned the identical symbols, and the description is omitted. The biological information display screens 334A and 334B include a variation display area 80.

In the variation display area 80, a 95% confidence interval (CI) is indicated as a value indicating the variation. Numerical values "±2" and "±5" indicated in the variation display area 80 are values that form the 95% confidence interval by adding the measured value of the respiratory rate (the value in the respiratory rate display area 75). That is, in a biological information display screen 334A, "12 to 16" obtained by adding "±2" to the measured value "14" of the respiratory rate form the 95% confidence interval. In a biological information display screen 334B, "9 to 19" obtained by adding "±5" to the measured value "14" of the respiratory rate form the 95% confidence interval.

In this example, the indicator ($2\sigma$ standard deviation) of the variation range is indicated. Accordingly, the user can clearly determine the range in which the measured value can reside. If the variation range is larger than a predetermined reference, the controller 31 colors the variation display area 80 with a color different from the color of the other areas, or displays the area in a blinking manner, thus attracting attention.

On the biological information display screen 334B, the variation display area 80 is colored, which indicates the reason of the low reliability degree "the variation in respiratory rate is large".

According to such displaying, the user can grasp that there is a possibility that an abnormality occurs in the measured value, confirm the situations of the patient, and review the measurement environment.

Here, if the reliability degree is determined to be low, the part (variation display area 80) of the biological information display screen 334B including the biological information is displayed in a display mode different from the mode before determination of the reliability degree to be low (see FIG. 13A). Alternatively, the entire biological information display screen 334B may be displayed in a display mode different from the mode before determination of the reliability degree to be low (the entire screen is displayed in a blinking manner, change in color, and the like). The display mode in the area out of the screen of the biological information display screen 334B may be displayed in a display mode different from the mode before determination of the reliability degree to be low (the area out of the screen is displayed in a blinking manner, change in color, and the like).

FIGS. 13A and 13B show the example of displaying the statistics indicating the variation irrespective of the magnitude of the variation in measured value. Alternatively, the display 33 may display the statistics, such as the standard deviation, and the variation coefficient, only if the variation in measured value is large.

If the reliability degree is determined to be low because the variation in measured value is large, the controller 31 may cause the display 33 to display not only the real-time measured value, but also a spectrum, a histogram, and a graph of time-series data indicating the variation in the measured value or the signal value, thus presenting the degree of variation to the user.

According to such display, the user can grasp the degree of variation, and determine a subsequent process in consideration of the state of the current patient state.

The spectrum display, or the histogram display can present the user with the distribution itself of the respiration signal components in a short time period. Even if the variation does not have a normal distribution, the component of the respiration signal of the patient can be directly, visually confirmed. By indicating the spectrum or the histogram in a time-series manner (adding the temporal axis, and achieving three-dimensional representation), for the patient performing characteristic respiration, it can be confirmed whether the characteristic component varies or not as time elapses. Preferably, the time-series display displays the position of the peak and the like in order to facilitate grasping of the temporal change in characteristic respiration component.

If the measurement target does not move (or has a small movement) or a predetermined S/N ratio is not achieved, it is preferable to perform display so that a state of leaving the bed, an infrequent respiration state, or an apneic state can be identified. Note that if it is determined to be "away from the bed" based on the output of the respiration sensor 42 (radio wave sensor), it can be important whether a large body motion is detected or not before reduction in S/N ratio, as an element of determining the state of being away from the bed. Accordingly, it is preferable to determine the state of being away from the bed, the infrequent respiration state, or the apneic state, in consideration of the temporal change in body motion, and its magnitude.

The controller 31 causes the radio wave respiration sensor 42 to achieve beam forming, and distance separation, clearly grasps presence or absence of a patient on the bed, and may adopt it as an element for determining whether the patient is away from the bed or not.

Figures 14, 15:
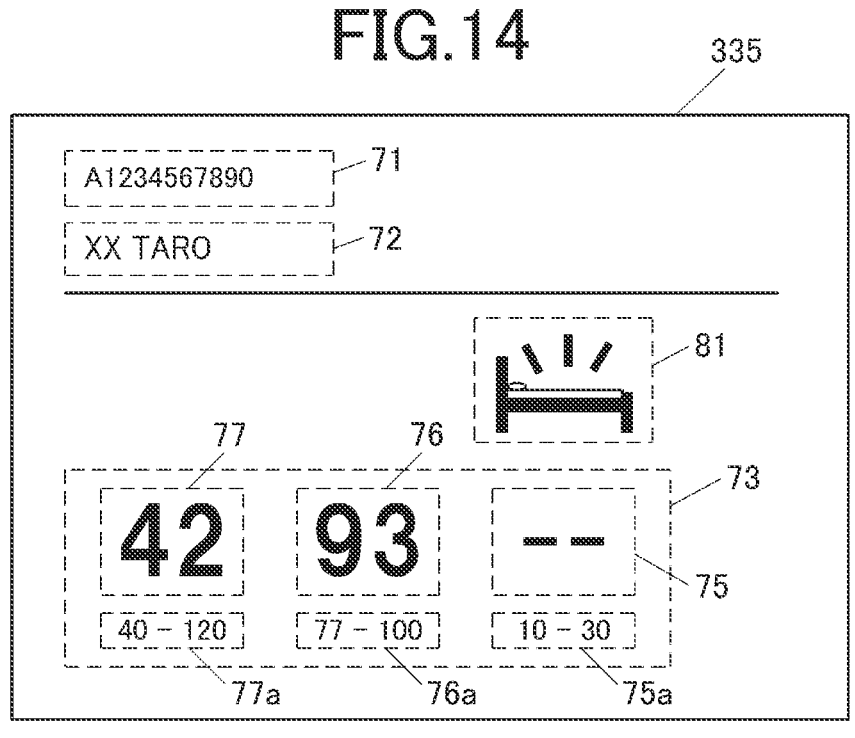
FIG. 14 shows an example of a biological information display screen including a bed leaving display.
FIG. 15 shows an example of a biological information display screen including a warning indicating that it is out of a measurement assurance range.

FIG. 14 shows an example of a biological information display screen 335 that includes a bed leaving display, and is displayed on the display 33. On the biological information display screen 335, components similar to those on the biological information display screen 331A (see FIG. 9A) are assigned the identical symbols, and the description is omitted. The biological information display screen 335 includes a bed leaving display area 81.

Upon determination of a state of being away from the bed, the controller 31 displays an image indicating the state of being away from the bed (the patient is away from the bed) in the bed leaving display area 81. In the biological information display screen 335, content indicated in the bed leaving display area 81 indicates the reason of the low reliability degree of the respiratory rate.

FIG. 15 shows an example of a biological information display screen 336 including a warning that indicates that it is out of a measurement assurance range, and is displayed on the display 33. The measurement assurance range is a range of the measured value secured for the measuring instrument (biological information detector 40, such as the pulse oximeter 41, and the respiration sensor 42). On the biological information display screen 336, components similar to those on the biological information display screen 331A (see FIG. 9A) are assigned the identical symbols, and the description is omitted.

If the measured value of the respiratory rate (the value of the respiratory rate display area 75) is out of the measurement assurance range, the controller 31 provides a red frame in the respiratory rate display area 75, and colors the respiratory rate display area 75, thus highlighting the area. The measurement assurance range is preliminarily stored in the storage 36 with respect to each type of the biological information.

Note that the reference range (normal range) indicated in a reference range display area 75a is set in the measurement assurance range.

On the biological information display screen 336, the antenna display in the signal quality display area 74 indicates that the intensity of the received signal of the respiration sensor 42 is sufficient, and the colored respiratory rate display area 75 indicates that the measured value of the respiratory rate is out of the measurement assurance range.

The radio wave respiration sensor 42 has a fault that it is difficult to identify whether a site to be measured is successfully measured, except for the case of being arranged adjacent to a site of the patient to be measured. The fault itself directly leads to the measurement reliability. Accordingly, if the required measurement accuracy cannot be achieved, the direction and distance to the currently measured site may be displayed on the screen.

Figures 16A, 16B:
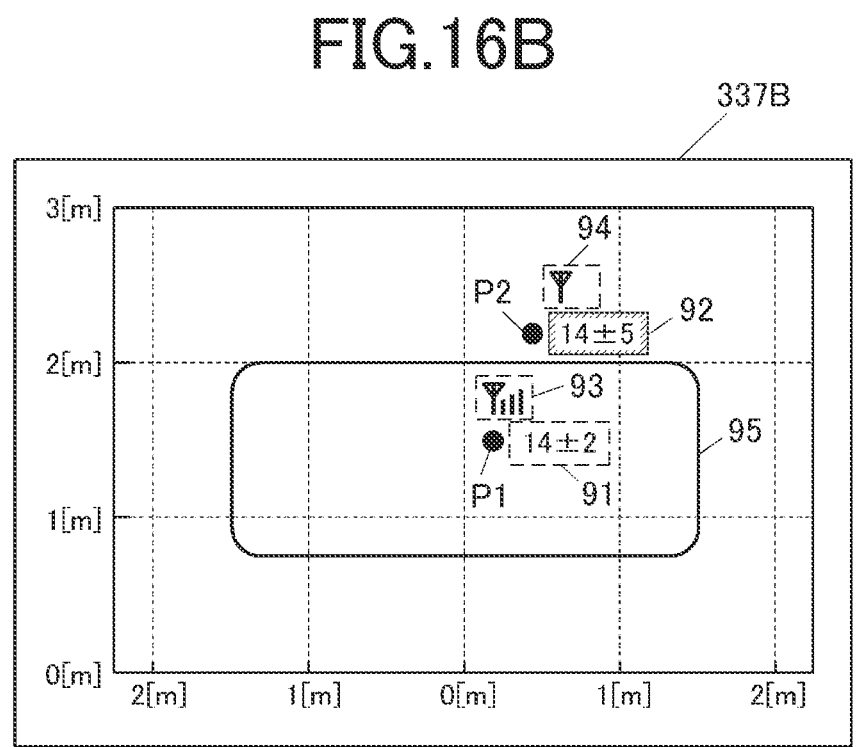
FIG. 16A shows an example of a measurement site display screen.
FIG. 16B shows an example of a measurement site display screen including a bed position.

FIG. 16A shows an example of a measurement site display screen 337A displayed on the display 33.

The controller 31 assumes the position of the respiration sensor 42 as an origin (0, 0) on the measurement site display screen 337A, draws the coordinates in the lateral direction (horizontal direction) on the abscissa axis, and in the front direction (distance direction) on the ordinate axis, and plots detected positions P1 and P2 of biosignals on the coordinates. It is shown that the detected position P2 is distant from the respiration sensor 42 in comparison with the detected position P1.

By drawing such coordinates, the user can correctly grasp the positional relationship about the measurement target from the respiration sensor 42.

Furthermore, a measured value display area 91 at the detected position P1, and a measured value display area 92 at the detected position P2 are provided on the measurement site display screen 337A.

The controller 31 displays the measured value of the respiratory rate detected at the detected position P1, with the variation (2a standard deviation) in the measured value display area 91. The controller 31 displays the measured value of the respiratory rate detected at the detected position P2, with the variation, in the measured value display area 92. The controller 31 colors the measured value display area 92 with a color different from that in the other areas in order to highlight the fact that the variation at the detected position P2 is large.

The reason of the low reliability degree "there are multiple measurement candidates" is displayed through presence of the detected positions P1 and P2 on the measurement site display screen 337A.

By the variation (±5) and coloring in the measured value display area 92, the reason of the low reliability degree of the respiratory rate "the variation in measured value is large" is displayed on the measurement site display screen 337A.

That is, on the measurement site display screen 337A, as for determination of the reliability degree of the biological information, the pieces of information related to multiple reasons of the determination results are displayed on the same screen of the display 33.

Preferably, to clarify the actual positional relationship of the measurement target in the patient room, the coordinates, and the layout of the patient room are displayed in an overlaid manner.

FIG. 16B shows an example of a measurement site display screen 337B where the bed position is displayed in combination with the coordinates described above. On the measurement site display screen 337B, the detected positions P1 and P2 of the biosignals are indicated. The measured value display area 91 at the detected position P1, the measured value display area 92 at the detected position P2, a signal level display area 93 at the detected position P1, and a signal level display area 94 at the detected position P2 are provided. The measured value display area 91, and the measured value display area 92 are similar to those in the measurement site display screen 337A.

The controller 31 displays the intensity of the signal received at the detected position P1, by the number of antennas, in the signal level display area 93. The controller 31 displays the intensity of the signal received at the detected position P2, by the number of antennas, in the signal level display area 94.

The controller 31 displays a bed position 95 indicating the position of the bed in the patient room, on the measurement site display screen 337B. Information indicating the bed position associated with the bedside terminal 30 is preliminarily stored in the storage 36.

On the measurement site display screen 337B, in addition to the reason of the low reliability degree similar to that in the measurement site display screen 337A, the reason of the low reliability degree of the respiratory rate "the signal received at the detected position P2 is low" is displayed by the antenna display in the signal level display area 94, and the reason of the low reliability degree of the respiratory rate "the detected position P2 is "the detected position P2 is out of the measurement target (bed position 95)" is displayed by the relationship between the detected position P2 and the bed position 95.

By such display, the user can intuitively grasp whether the measurement is appropriate (whether the measured value is a reliable value), and whether the measurement target is correct.

If the measurement site is different from an intended site when such display is presented to the user, the intended target can be measured by clearly limiting the angle and distance to be measured, through an instruction by the user from the operation receiver 32.

If multiple pieces of biological information are detected by the radio wave respiration sensor 42, the controller 31 may reflect how the detected position is close to a predefined area (for example, on the bed etc.), and to a specific position in the area (for example, around the position of the chest), as parameters, in reliability determination.

Figure 17:
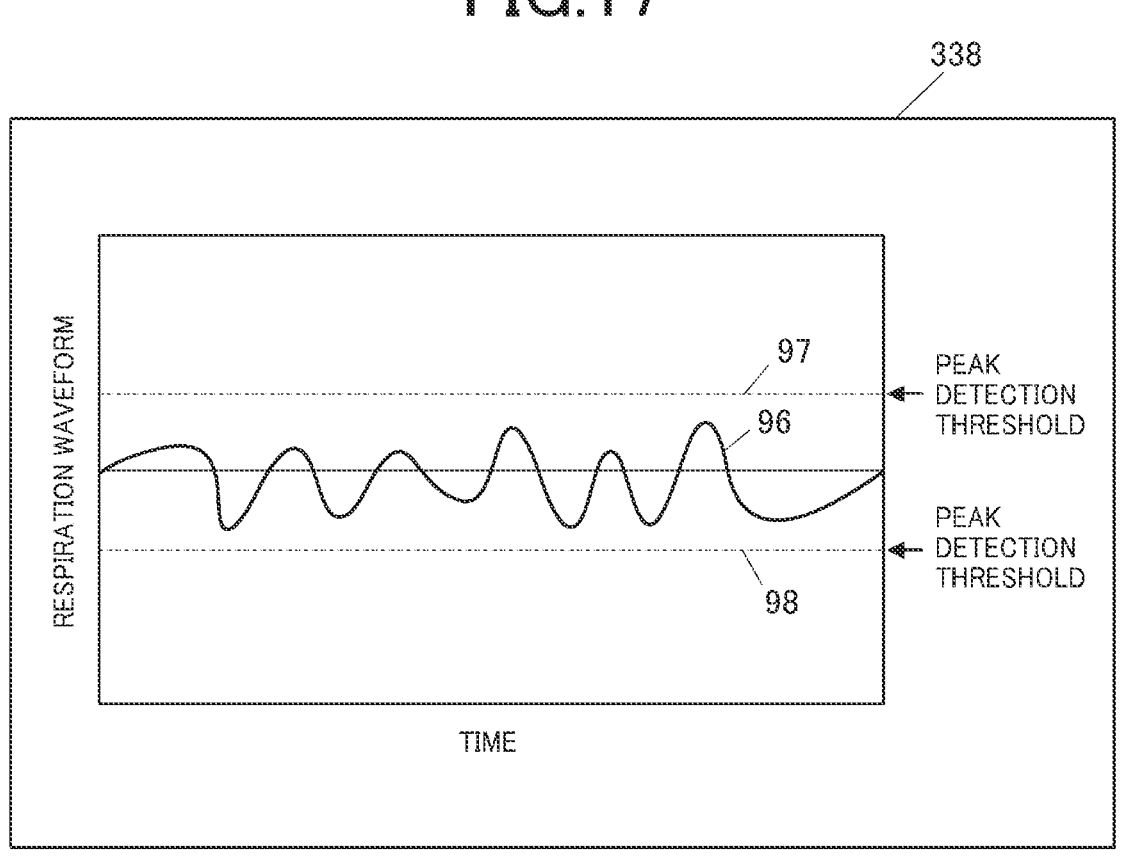
FIG. 17 shows an example of a respiratory waveform display screen.

FIG. 17 shows an example of a respiratory waveform display screen 338 displayed on the display 33.

The controller 31 displays a respiratory waveform 96 on the respiratory waveform display screen 338. The respiratory waveform 96 is a graph where the respiration signal is plotted along a lapse of time. As shown in FIG. 17, with the respiratory waveform 96, peak detection thresholds 97 and 98 may be indicated by dotted lines. The peak detection thresholds 97 and 98 are thresholds used to detect a peak from the respiration signal. If the signal value of the respiratory waveform 96 becomes equal to or higher than the peak detection threshold 97, it is determined as a peak that is convex upward. If the signal value of the respiratory waveform 96 becomes equal to or lower than the peak detection threshold 98, it is determined as a peak convex downward. On the respiratory waveform display screen 338, inclusion of the respiratory waveform 96 between the peak detection threshold 98 and the peak detection threshold 97 displays the reason of the low reliability degree "the amplitude of the respiration signal is small (respiration is shallow) ".

As described above, according to this embodiment, the controller 31 of the bedside terminal 30 causes the display 33 to display the information related to the reason of the determination result of the reliability degree of the biological information. Accordingly, to determine the reliability degree of the biological information, the information for recognizing the reason of the determination result can be provided.

In particular, if the reliability degree is determined to be low, the controller 31 causes the display 33 to display the information related to the reason of the low reliability degree. Accordingly, information for allowing the user to understand the reliability degree and take an action suitable for the current situations and environment can be provided.

The controller 31 causes the display 33 to display the information related to the reason of the determination result in the display mode in accordance with the reason of the determination result. Accordingly, the user can easily recognize the reason of the determination result through the display mode, and can appropriately take effective measures.

The controller 31 causes the display 33 to display the reliability degree itself of the biological information, which can directly provide the reliability degree to the user.

The controller 31 displays the pieces of information related to the reasons of the determination results, on the same screen of the display 33, which can efficiently provide the information to the user.

If the reliability degree is determined to be low, the controller 31 causes the display 33 to display the measures against the reason of the low reliability degree. Thus, what should be done to improve the reliability degree can be presented to the user.

If the reliability degree is determined to be low, the controller 31 causes the display mode on the display 33 (part or the entirety of the display screen (biological information display screen etc.), an area out of the screen, etc.) to the display mode different from the mode before determination of the reliability degree to be low, thus allowing the user to be notified that the reliability degree of the biological information is low, and the situations are changed.

If the reason of the determination result is a reason caused by the living body of the patient, the reliability degree of the biological information can be improved by adjusting the positional relationship between the position of the living body and the measuring instrument (biological information detector 40), or by waiting until the body motion settles.

If the reason of the determination result is a reason other than what is caused by the living body of the patient, the reliability degree of the biological information can be improved by removing an obstacle between the position of the living body and the measuring instrument (biological information detector 40), or by changing the thresholds used to determine the reliability degree of the biological information.

If continuous occurrence of the body motion for a long time period is detected by the received signal obtained from the respiration sensor 42, the controller 31 may cause the display 33 to display the occurrence of the body motion, and the continuous duration.

Modification 1

Next, Modification 1 is described. Hereinafter, the difference from the embodiment described above is mainly described.

If the reason of the determination result of the reliability degree of the biological information includes at least a first reason and a second reason, the controller 31 of the bedside terminal 30 causes the display 33 to display information related to the first reason, and information related to the second reason, in a switchable manner.

Figure 18A:
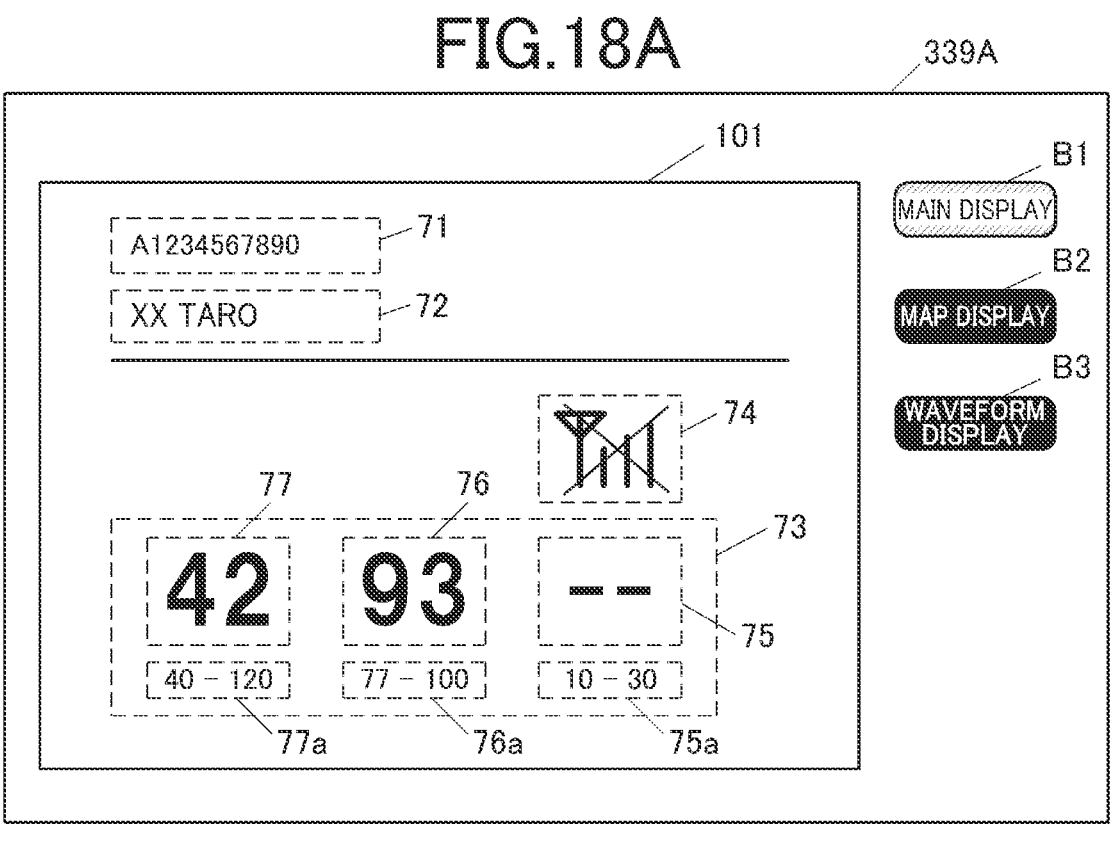
FIG. 18A shows an example of a main display screen in Modification 1.
Figure 18B:
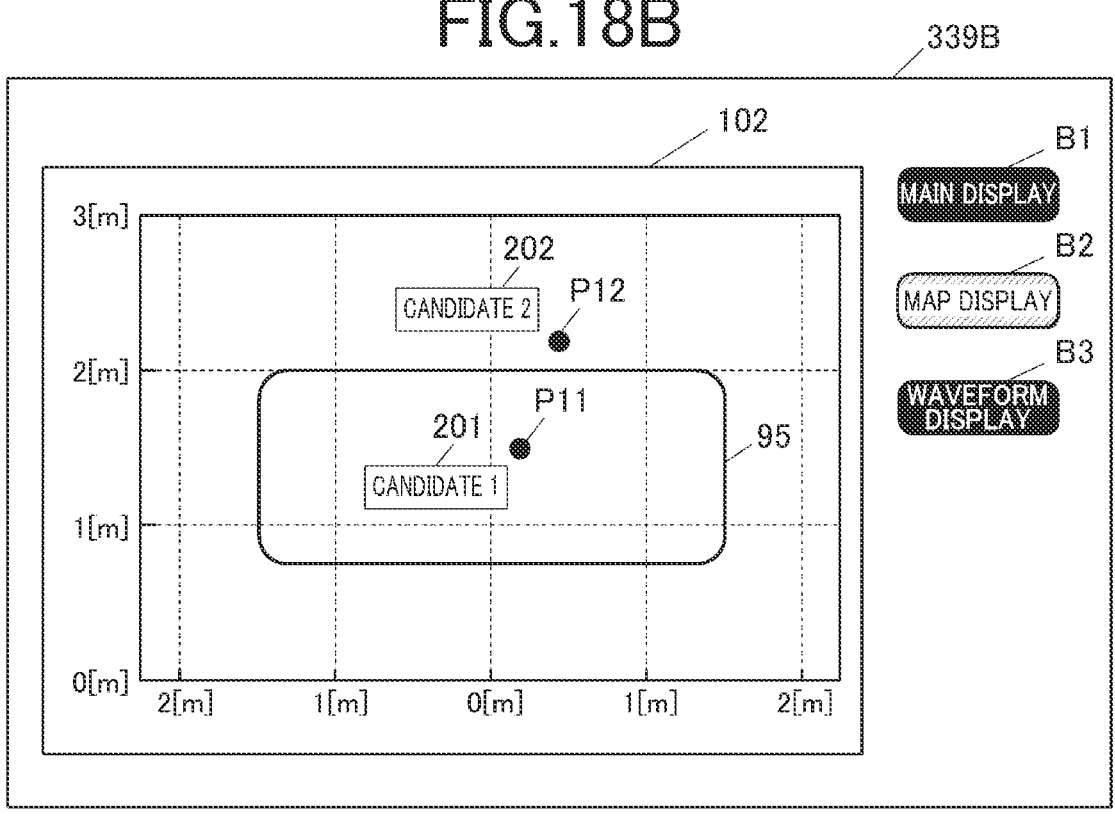
FIG. 18B shows an example of a map display screen in Modification 1.
Figure 18C:
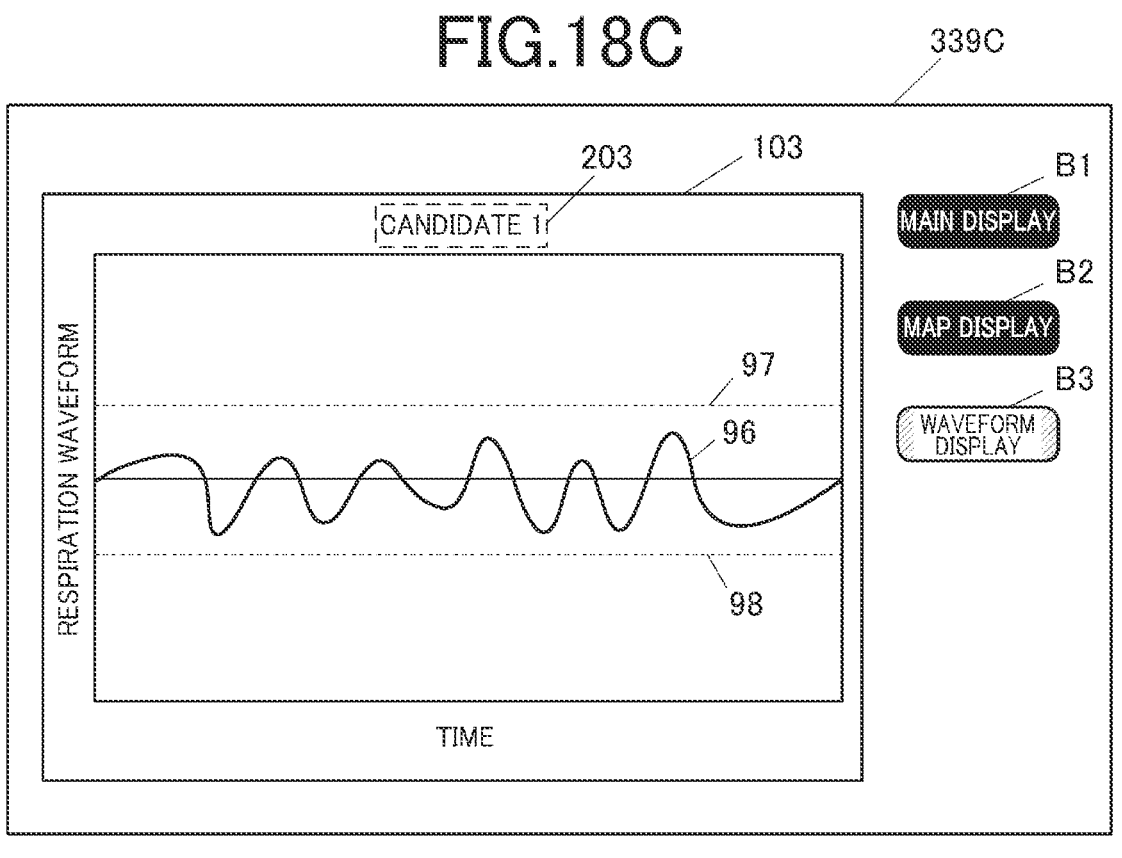
FIG. 18C shows an example of a waveform display screen in Modification 1.

FIGS. 18A, 18B, and 18C respectively show examples of a main display screen 339A, a map display screen 339B, and a waveform display screen 339C, which are displayed on the display 33 of the bedside terminal 30. The main display screen 339A, the map display screen 339B, and the waveform display screen 339C each include a main display button B1, a map display button B2, and a waveform display button B3.

On the main display screen 339A shown in FIG. 18A, the main display button B1 is in a selected state. This screen includes a biological information display area 101.

In the biological information display area 101, components similar to those on the biological information display screen 331C (see FIG. 9C) are assigned the identical symbols, and the description is omitted. In the signal quality display area 74 in the biological information display area 101, x (a cross mark) is displayed over the state with three standing antennas, thus indicating the reason of the low reliability degree "the received signal is too high" with respect to measurement of the respiratory rate.

On the map display screen 339B shown in FIG. 18B, the map display button B2 is in a selected state. This screen includes a measurement site display area 102.

In the measurement site display area 102, the position of the respiration sensor 42 is assumed as an origin (0, 0), the coordinates in the lateral direction (horizontal direction) are drawn on the abscissa axis, the coordinates in the front direction (distance direction) are drawn on the ordinate axis, and detected positions P11 and P12 of biosignals are plotted on the coordinates. In the measurement site display area 102, labels 201 and 202 for discriminating "CANDIDATE 1" and "CANDIDATE 2" are respectively displayed adjacent to the detected positions P11 and P12. In the measurement site display area 102, the bed position 95 is indicated. On the measurement site display area 102, the reasons of the low reliability degree of the respiratory rate including "there are multiple measurement candidates", "the measurement target at the detected position P12 is distant", and "the detected position P12 is off the bed position 95" are indicated by displaying the position of the measurement target including the distance, and the angle.

On the waveform display screen 339C shown in FIG. 18C, the waveform display button B3 is in a selected state. This screen includes a respiratory waveform display area 103.

In the respiratory waveform display area 103, components similar to those on the respiratory waveform display screen 338 (see FIG. 17) are assigned the identical symbols, and the description is omitted. In the respiratory waveform display area 103, a label 203 indicating that the respiratory waveform 96 is associated with "CANDIDATE 1" (the measurement result at the detected position P11 shown in FIG. 18B) is added. In the respiratory waveform display area 103, the respiratory waveform 96 indicates the reason of the low reliability degree "the amplitude of the respiration signal is small (respiration is shallow)".

When the map display button B2 is pressed by operation on the operation receiver 32 (touch panel) on the main display screen 339A or the waveform display screen 339C, the controller 31 switches the screen to be displayed on the display 33, to the map display screen 339B.

When the waveform display button B3 is pressed by operation on the operation receiver 32 on the main display screen 339A or the map display screen 339B, the controller 31 switches the screen to be displayed on the display 33, to the waveform display screen 339C.

When the main display button B1 is pressed by operation on the operation receiver 32 on the map display screen 339B or the waveform display screen 339C, the controller 31 switches the screen to be displayed on the display 33, to the main display screen 339A.

According to Modification 1, in a case where there are multiple reasons of the determination result with respect to determination of the reliability degree of the biological information, the controller 31 of the bedside terminal 30 can cause the display 33 to display the information related to the multiple reasons of the determination result in a switchable manner. The screens suitable for the respective reasons are switched depending on each reason of determination result of the reliability degree. Accordingly, the user can more deeply recognize each reason.

Note that according to Modification 1, in accordance with manual operation by the user on the operation receiver 32, the information related to the multiple reasons of the determination result are switched. Alternatively, the information related to the multiple reasons of the determination result may be switched at predetermined time intervals.

Modification 2

Next, Modification 2 is described. Hereinafter, the difference from the embodiment described above is mainly described.

If the reason of the determination result of the reliability degree of the biological information includes at least a first reason and a second reason, the controller 31 of the bedside terminal 30 displays information related to the first reason, and information related to the second reason, in display areas on the display 33 that are different from each other.

Figure 19:
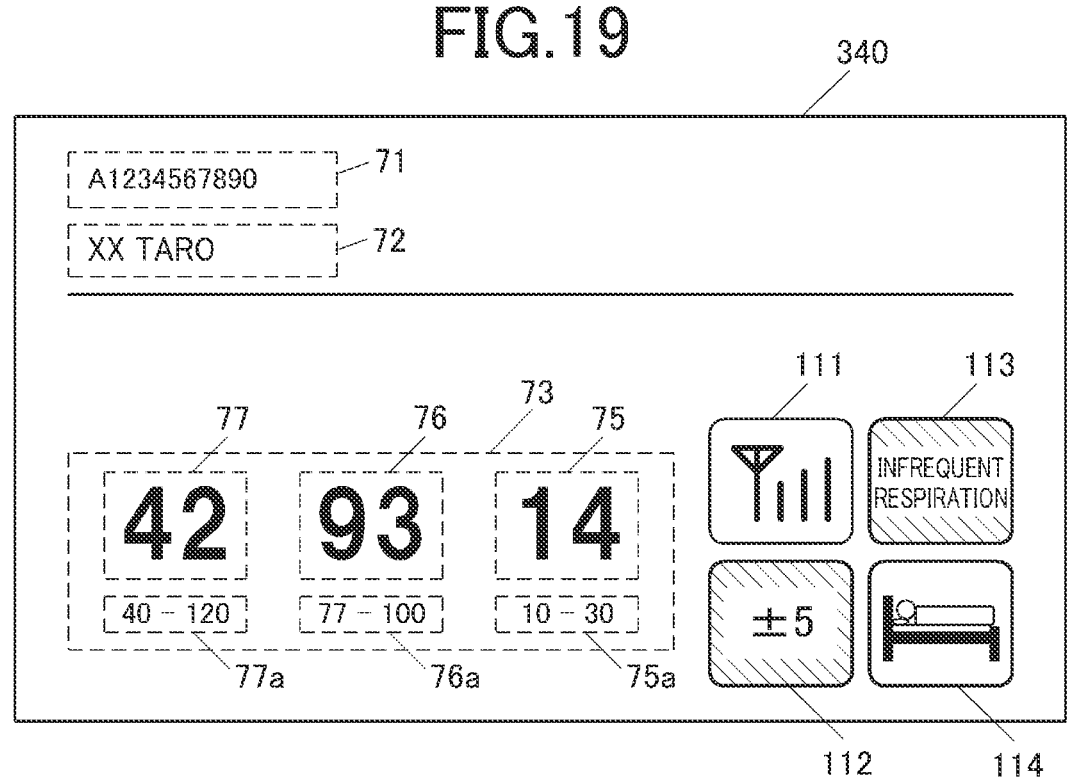
FIG. 19 shows an example of a biological information display screen in Modification 2.

FIG. 19 shows an example of a biological information display screen 340 displayed on the display 33 of the bedside terminal 30. On the biological information display screen 340, components similar to those on the biological information display screen 331A (see FIG. 9A) are assigned the identical symbols, and the description is omitted. The biological information display screen 340 includes a signal quality display area 111, a variation display area 112, an infrequent respiration display area 113, and a bed leaving/bed rest display area 114.

In the signal quality display area 111, the intensity of the received signal of the respiration sensor 42 (radio wave sensor) is displayed in a four-staged manner.

In the variation display area 112, the variation ($2a$ standard deviation etc.) of the respiratory rate (the value in the respiratory rate display area 75) is displayed. On the biological information display screen 340, the variation display area 112 is colored to be identifiable from the other area, thus displaying the reason of the low reliability degree "the variation in respiratory rate is large".

In the infrequent respiration display area 113, the reason of the low reliability degree "the patient is in an infrequent respiration state" with respect to the measured value of the respiratory rate is displayed. The infrequent respiration display area 113 is colored with a color different from that in the other areas, thus highlighting the fact that the reliability degree of the respiratory rate is low.

In the bed leaving/bed rest display area 114, an image indicating whether the patient is in the bed leaving state, or the bed rest state is displayed. In the bed leaving/bed rest display area 114 on the biological information display screen 340, "the patient is in the bed rest state" is displayed.

According to Modification 2, if there are multiple reasons of the determination result with respect to the determination of the reliability degree of the biological information, the controller 31 of the bedside terminal 30 displays the information related to the multiple reasons of the determination results, on display areas (the variation display area 112, and the infrequent respiration display area 113) on the display 33 that are different from each other, which can display the reasons in a discriminated manner, and efficiently provide the information to the user.

The description in the embodiment, and Modifications 1 and 2 described above are on examples of the biological information monitoring apparatus, the biological information monitoring system, the biological information monitoring program, and the biological information monitoring method according to the present invention, but these examples do not limit the invention. Detailed configurations and detailed operation of the components constituting each apparatus can be changed as appropriate within a range not deviating from the spirit of the present invention.

For example, according to the embodiment, and Modifications 1 and 2 described above, description has been made in the case where the bedside terminal 30 includes: the obtainer that obtains the biological information on the patient; the reliability degree determiner that determines the reliability degree of the biological information: the reason deriver that derives the reason of the determination result of the reliability degree of the biological information; and the display controller that causes the display to display the information related to the reason of the determination result. Alternatively, each of the functional components, which are the obtainer, the reliability degree determiner, the reason deriver, and the display controller, may be included in any apparatus in the biological information monitoring system 100. Specifically, the bedside terminal 30 may obtain the determination result of the reliability degree, and the reason of the determination result, from an external apparatus, such as the station server 10, or the mobile terminal 60, and use the reasons for display.

According to the embodiment, and Modifications 1 and 2 described above, the case of displaying the biological information on the patient associated with the bedside terminal 30, and the information related to the reason of the determination result of the reliability degree, on the display 33 of the bedside terminal 30 is described as the example. Alternatively, biological information on multiple patients, and information related to the reason of the determination result of the reliability degree may be displayed on the monitoring screen displayed on the display 13 of the station server 10. In this case, the controller 31 of the bedside terminal 30 may generate screen data for displaying various screens on the display 13 of the station server 10, and transmit the data to the station server 10 through the wireless communicator 35. The controller 11 of the station server 10 may generate the screen data for displaying various screens on the display 13, based on information obtained from the bedside terminal 30 through the wireless communicator 14 (the biological information, and the information related to the reason of the determination result of the reliability degree).

Alternatively, biological information on one or more patients, and the information related to the reason of the determination result of the reliability degree may be displayed on the display 63 of the mobile terminal 60 carried by a healthcare worker, such as a nurse. In this case, the controller 31 of the bedside terminal 30 may generate screen data for displaying various screens on the display 63 of the mobile terminal 60, and transmit the data to the mobile terminal 60 through the wireless communicator 35. Alternatively, the controller 61 of the mobile terminal 60 may generate image data for displaying various screens on the display 63, based on the information obtained from the bedside terminal 30 through the wireless communicator 64 (the biological information, and the information related to the reason of the determination result of the reliability degree).

The biological information detector 40, which pertains to the biological information serving as the determination target of the reliability degree, is not limited to a non-contact sensor. In view of difficulty in obtaining the reliability, the present invention is particularly important for the non-contact sensor.

According to the embodiment, and Modifications 1 and 2 described above, the respiratory rate is mainly described as the biological information. However, the biological information serving as the determination target of the reliability degree may be biological information other than the respiratory rate, for example, the heart rate, SpO$_2$, pulse rate, etc.

The program for executing each process in each apparatus may be stored in a portable recording medium. Further, as a medium that provides data of the program via a communication line, a carrier wave may be applied.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A biological information monitoring apparatus, comprising a hardware processor that:

obtains biological information on a patient, wherein at least one of a respiratory rate, a percutaneous oxygen saturation (SpO$_2$), or a pulse rate is obtained by a pulse oximeter or a respiration sensor as the biological information;

determines a reliability degree of the biological information, wherein the reliability degree is calculated by comparing a received power when receiving the biological information, a magnitude of phase variation, or statistics of the biological information with a threshold; and causes a display to display information related to a reason of the calculated reliability degree, wherein upon determination that the reliability degree is lower than a predetermined reference, the hardware processor causes the display to display information related to a reason of a low reliability degree and an action to be taken against the reason of the low reliability degree, in a display mode in accordance with the reason of the low reliability degree, and wherein the reason of the low reliability degree is a problem of disturbing measurement to obtain the biological information, and the action is configured to remove the problem, and wherein the hardware processor is capable of determining multiple reasons of the low reliability degree for a single item of the biological information and causing the display to display information corresponding to each of the multiple reasons of the low reliability degree.

2. The biological information monitoring apparatus according to claim 1, wherein the reason of the calculated reliability degree is a reason caused by a living body of the patient, or a reason caused by what is other than the living body of the patient.

3. The biological information monitoring apparatus according to claim 1, wherein the hardware processor derives the reason of the calculated reliability degree.

4. The biological information monitoring apparatus according to claim 1, wherein the hardware processor further causes the display to display the reliability degree.

5. The biological information monitoring apparatus according to claim 1, wherein the reason of the calculated reliability degree includes at least a first reason, and a second reason, and the hardware processor causes the display to display information related to the first reason, and the information related to the second reason in a switchable manner.

6. The biological information monitoring apparatus according to claim 1, wherein the reason of the calculated reliability degree includes at least a first reason, and a second reason, and the hardware processor displays the information related to the first reason, and the information related to the second reason, respectively in display areas on the display that are different from each other.

7. The biological information monitoring apparatus according to claim 1, wherein the reason of the calculated reliability degree includes at least a first reason, and a second reason, and the hardware processor causes the display to display information related to the first reason, and the information related to the second reason, on an identical screen of the display.

8. The biological information monitoring apparatus according to claim 1, wherein upon determination that the reliability degree is lower than the predetermined reference, the hardware processor causes the display to be in the display mode different from a mode before determination of the reliability degree to be lower than the predetermined reference.

9. The biological information monitoring apparatus according to claim 1, further comprising a notifier that issues a notification about the determination result when the hardware processor determines that the reliability degree is lower than the predetermined reference.

10. A biological information monitoring system, comprising a hardware processor that:

obtains biological information on a patient, wherein at least one of a respiratory rate, a percutaneous oxygen saturation (SpO$_2$), or a pulse rate is obtained by a pulse oximeter or a respiration sensor as the biological information;

determines a reliability degree of the biological information, wherein the reliability degree is calculated by comparing a received power when receiving the biological information, a magnitude of phase variation, or statistics of the biological information with a threshold; and causes a display to display information related to a reason of the calculated reliability degree, wherein upon determination that the reliability degree is lower than a predetermined reference, the hardware processor causes the display to display information related to a reason of a low reliability degree and an action to be taken against the reason of the low reliability degree, in a display mode in accordance with the reason of the low reliability degree, wherein the reason of the low reliability degree is a problem of disturbing measurement to obtain the biological information, and the action is configured to remove the problem, and wherein the hardware processor is capable of determining multiple reasons of the low reliability degree for a single item of the biological information and causing the display to display information corresponding to each of the multiple reasons of the low reliability degree.

11. The biological information monitoring system according to claim 10, wherein the hardware processor derives the reason of the calculated reliability degree.

12. A computer-readable non-transitory recording medium storing a biological information monitoring program that causes a computer to achieve:

an obtainment function of obtaining biological information on a patient, wherein at least one of a respiratory rate, a percutaneous oxygen saturation (SpO$_2$), or a pulse rate is obtained by a pulse respiration sensor as the biological information;

a reliability degree determination function of determining a reliability degree of the biological information, wherein the reliability degree is calculated by comparing a received power when receiving the biological information, a magnitude of phase variation, or statistics of the biological information with a threshold; and a display control function of causing a display to display information related to a reason of a calculated reliability degree by the reliability degree determination function, wherein upon determination that the reliability degree is lower than a predetermined reference, the display control function causes the display to display information related to a reason of a low reliability degree and an action to be taken against the reason of the low reliability degree, in a display mode in accordance with the reason of the low reliability degree, wherein the reason of the low reliability degree is a problem of disturbing measurement to obtain the biological information, and the action is configured to remove the problem, and wherein the hardware processor is capable of determining multiple reasons of the low reliability degree for a single item of the biological information and causing the display to display information corresponding to each of the multiple reasons of the low reliability degree.

13. A biological information monitoring method, comprising:

obtaining biological information on a patient, wherein at least one of a respiratory rate, a percutaneous oxygen saturation (SpO$_2$), or a pulse rate is obtained by a pulse oximeter or a respiration sensor as the biological information;

determining a reliability degree of the biological information, wherein the reliability degree is calculated by comparing a received power when receiving the biological information, a magnitude of phase variation, or statistics of the biological information with a threshold; and causing a display to display information related to a reason of a calculated reliability degree by the reliability degree determining, wherein upon determination that the reliability degree is lower than a predetermined reference, the display is caused to display information related to a reason of a low reliability degree and an action to be taken against the reason of the low reliability degree, in a display mode in accordance with the reason of the low reliability degree, wherein the reason of the low reliability degree is a problem of disturbing measurement to obtain the biological information, and the action is configured to remove the problem, and wherein the hardware processor is capable of determining multiple reasons of the low reliability degree for a single item of the biological information and causing the display to display information corresponding to each of the multiple reasons of the low reliability degree.

14. The biological information monitoring apparatus according to claim 1, wherein the biological information is obtained by the respiration sensor, and the respiration sensor is a radio wave sensor emitting a radio wave and receiving the radio wave reflected by a measurement target object.

* * * * *